United States Patent
Vukasinovic et al.

(10) Patent No.: US 7,855,070 B2
(45) Date of Patent: Dec. 21, 2010

(54) CENTIMETER-SCALE, INTEGRATED DIAGNOSTICS INCUBATOR FOR BIOLOGICAL CULTURING

(75) Inventors: Jelena Vukasinovic, Atlanta, GA (US); Ari Glezer, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 923 days.

(21) Appl. No.: 11/483,126

(22) Filed: Jul. 7, 2006

(65) Prior Publication Data
US 2007/0128715 A1    Jun. 7, 2007

Related U.S. Application Data

(60) Provisional application No. 60/697,437, filed on Jul. 8, 2005.

(51) Int. Cl.
*C12M 1/00* (2006.01)
*C12M 3/00* (2006.01)

(52) U.S. Cl. ................................ 435/293.1; 435/303.1

(58) Field of Classification Search ... 435/293.1–294.1, 435/303, 289.1, 303.1
See application file for complete search history.

(56) References Cited

U.S. PATENT DOCUMENTS

| | | | |
|---|---|---|---|
| 4,572,427 A * | 2/1986 | Selfridge et al. ................ | 236/3 |
| 5,090,617 A * | 2/1992 | Swan et al. ..................... | 236/3 |
| 5,879,876 A | 3/1999 | Wolfinbarger, Jr. et al. | |
| 5,882,918 A * | 3/1999 | Goffe ....................... | 435/286.6 |
| 6,057,150 A | 5/2000 | Lee et al. | |
| 6,197,575 B1 | 3/2001 | Griffith et al. | |
| 6,368,838 B1 | 4/2002 | Singhvi et al. | |
| 6,503,751 B2 | 1/2003 | Hugh | |
| 6,521,451 B2 | 2/2003 | Potter | |
| 6,705,357 B2 | 3/2004 | Jeon et al. | |
| 7,056,726 B2 * | 6/2006 | Legeay et al. ............ | 435/297.1 |
| 7,270,996 B2 * | 9/2007 | Cannon et al. ........... | 435/293.1 |
| 7,462,484 B2 * | 12/2008 | Mizuno ..................... | 435/372 |
| 2002/0110905 A1 * | 8/2002 | Barbera-Guillem et al. ...... | 435/294.1 |
| 2003/0004394 A1 | 1/2003 | Carpay | |
| 2004/0132175 A1 | 7/2004 | Vetillard et al. | |

(Continued)

OTHER PUBLICATIONS

International Search Report and Written Opinion on co-pending, related PCT Application No. PCT/US2007/072777, mailed Jul. 25, 2008.

(Continued)

*Primary Examiner*—Walter D Griffin
*Assistant Examiner*—Shanta G Doe
(74) *Attorney, Agent, or Firm*—Thomas, Kayden, Horstemeyer & Risley, LLP

(57) ABSTRACT

Disclosed are portable, disposable, centimeter-scale, integrated diagnostics incubators for use in biological culturing. An exemplary incubator comprises an optically accessible enclosure having a plurality of fluidic ports. A heating element is disposed within the enclosure that is coupled to an external heater controller. An autoclavable microfluidic perfusion chamber is disposed within the enclosure that comprises a cell culture life support chamber, an inlet port disposed in the perfusion chamber, a collection chamber in communication with the culture chamber, an outlet port coupled to the collection pool, and a perfusing substrate. An optically transparent, gas permeable membrane is attachable to the top of the perfusion chamber. The incubators have optical accessibility, forced flow fluidic control, temperature control, are portable and modular, and are inexpensively manufactured. The incubators permit in-the-field drug testing and culturing of biological tissues.

33 Claims, 8 Drawing Sheets

U.S. PATENT DOCUMENTS

| | | | |
|---|---|---|---|
| 2005/0089993 | A1 | 4/2005 | Boccazzi et al. |
| 2005/0112759 | A1 | 5/2005 | Radisic et al. |
| 2005/0186671 | A1 | 8/2005 | Cannon et al. |
| 2005/0221269 | A1 | 10/2005 | Taylor et al. |
| 2006/0073539 | A1 | 4/2006 | Wikswo et al. |

OTHER PUBLICATIONS

Grinnel, Frederick, "Fibroblast-Collagen-Matrix Contraction: Growth-Factor Signalling and Mechanical Loading," Trends in Cell Biology (vol. 10) Sep. 2000, pp. 362-365.

Wang, Fei; Weaver; Valerie M.; Petersen, Ole W.; Larabell, Carolyn A.; Dedhar, Shoukat; Briand, Per; Lupu, Ruth; Bissell, Mina J., "Reciprocal Interactions Between /31-Integrin and Epidermal Growth Factor Receptor in Three-Dimensional Basement Membrane Breast Cultures: A Different Perspective in Epithelial Biology," The National Academy of Sciences, Jun. 12, 1998, pp. 14821-14826.

O'Connor, Stephen; Stenger, David A.; Shaffer, Kara M.; Ma, Wu, "Survival and Neurite Outgrowth of Rat Cortical Neurons in Three-Dimensional Agarose and Collagen Gel Matrices," May 2001, Elsevier Science Ireland ltd., pp. 189-193.

Woerly, Stephane; Plant, Giles W.; Harvey, Alan R., "Cultured Rat Neuronal and Glial Cells Entrapped Within Hydrogel Polymer Matrices: A Potential Tool for Neural Tissue Replacement," Mar. 1996, Elsevier Science Ireland Ltd., pp. 197-201.

Haas, H.L.; Schaerer, B.; Vosmansky, M., "A Simple Perfusion Chamber for the Study of Nervous Tissue Slices in Vitro," Journal of Neuroscience Methods Dec. 1979, pp. 323-325.

Li, Choh-Luh; McIlwain, H., "Maintenance of Resting Membrane Potentials in Slices of Mammalian Cerebral Cortex and Other Tissues," National Institute of Neurological Diseases and Blindness, National Institutes of Health and Department of Biochemistry, Institute of Psychiatry (University of London), Dec. 1957, pp. 178-190.

Krimer, Leonid S.; Goldman-Rakic, Patricia S., "An Interface Holding Chamber for Anatomical and Physiological Studies of Living Brain Slices," Journal of Neuroscience Methods Jul. 1997, pp. 55-58.

Croning, M.D.R.; Haddad, G.G., "Comparison of Brain Slice Chamber Designs for Investigations of Oxygen Deprivation in Vitro," Journal of Neuroscience Methods Jun. 1998, pp. 103-111.

Xia, Younan; Whitesides, George M., "Soft Lithography," Angewandte Chemie Ed., Jan. 1998, pp. 550-575.

Ng, Jessamine M.K.; Gitlin, Irina; Stroock, Abraham D.; Whitesides, George M., "Components for Integrated Poly(dimethylsiloxane) Microfluidic Systems," Electrophoresis Oct. 2002, pp. 3461-3473.

McDonald, J. Cooper; Whitesides, George M., "Poly(dimethylsiloxane) as a Material for Fabricating Microfluidic Devices," American Chemical Society, Jul. 2002, pp. 491-499.

Whitesides, George M.; Ostuni, Emanuele; Takayama, Shuichi; Jiane, Xingyu; Ingber, Donald E., "Soft Lithography in Biology and Biochemistry," Annual Review Biomed, Aug. 2001, pp. 335-375.

Harsch, A.; Calderon, J.; Timmons, R.B.; Gross, G.W., "Pulsed Plasma Deposition of Allylamine on Polysiloxane: A Stable Surface for Neuronal Cell Adhesion," Journal of Neuroscience Methods Jun. 2000, pp. 135-144.

Bernard, A.; Fitzli, Dora; Sonderegger, Peter; Delamarche, Emmanuel; Michel, Bruno; Bosshard, Hans Rudolf; Biebuyck, Hans, "Affinity Capture of Proteins from Solution and Their Dissociation by Contact Printing," Nature Biotechnology, vol. 19, Sep. 2001, pp. 866-869.

Donzel, Christian; Geissler, Matthias; Bernard, Andre; Wolf, Heiko; Michel, Wolf; Hilborn, Jons; Delamarche, Emmanuel, "Hydrophilic Poly(dimethylsiloxane) Stamps for Microcontact Printing," Advanced Materials 13, No. 15, Aug. 2001, pp. 1164-1168.

Beebe, David J.; Moore, Jeffrey S.; Yu, Qing; Liu, Robin H.; Kraft, Mary L.; Jo, Byung-Ho; Devadoss, Chelladurai, "Microfluidic Tectonics: A Comprehensive Construction Platform for Microfluidic Systems," Proc. National Academy of Science, Dec. 2000, pp. 13488-13493.

Chaginyc, Michael L.; Chiu, Daniel T.; McDonald, J. Cooper; Stroock, Abraham D.; Christian, James F.; Karger, Arieh M.; Whitesides, George M., "An Integrated Fluorescence Detection System in Poly (dimethylsiloxane) for Microfluidic Applications," Analytical Chemistry, vol. 73, No. 18, Sep. 2001, pp. 4491-4498.

Zanzotto, Andrea; Szita, Nicholas; Boccazzi, Paolo, Lessard, Philip; Sinskey, Anthony J.; Jensen, Klavs F., "Membrane-Aerated Microbioreactor for High-Throughput Bioprocessing," Wiley InterScience, Jun. 2004, pp. 243-254.

Cullen, D. Kacy; Vukasinovic, Jelena; Glezer, Ari; Laplaca, Michelle C., "High Cell Density Three-Dimensional Neural Co-Cultures Require Continuous Medium Perfusion for Survival," Annual International Conference IEEE, Apr. 2006.

Deshpande, Mohan; Vaishnav, Ramesh N., "Submerged Laminar Jet Impingement on a Plane," J. Fluid Mechanical, Jan. 1982, vol. 114, pp. 213-236.

Cullen, D. Kacy; Vukasinovic, Jelena; Glezer, Ari; Laplaca, Michelle C., "Microfluidic Engineered High Cell Density Three-Dimensional Neural Cultures," J. Neural Eng., Apr. 2007, pp. 159-172.

Potter, Steve M.; Demarse, Thomas B., "A New Approach to Neural Cell Culture for Long-Term Studies," Journal of Neuroscience Methods 110, Sep. 2001, pp. 17-24.

Prokop, Ales; Prokop, Zdenka; Schaffer, David; Kozlov, Eugene; Wikswo, John; Cliffel, David; Baudenbacher, Franz, "NanoLiterBioReactor: Long-Term Mammalian Cell Culture at Nanofabricated Scale," Biomedical Microdevices 6:4, Jan. 2004, pp. 325-339.

Granet, C.; Laroche, N.; Vico, I.; Alexandre, C.; Lafage-Proust, M.H., "Rotating-Wall Vessels, Promising Bioreactors for Osteoblastic Cell Culture: Comparison with Other 3D Conditions," Medical and Biological Engineering & Computing, Jul. 1998, pp. 513-519.

Rowe, Laura; Almasri, Mahmoud; Lee, Kil; Fogleman, Nick; Brewer, Gregory J.; Nam, Yoonkey; Wheeler, Bruce C.; Vukasinovic, Jelena; Glezer, Ari; Frazier, A. Bruno, "Active 3-D Microscaffold System with Fluid Perfusion for Culturing in Vitro Neuronal Networks," The Royal Society of Chemistry, Lab Chip, Apr. 2007, pp. 475-482.

Rajaraman, Swaminathan; Choi, Seong-O; Shafer, Richard H.; Ross, James D.; Vukasinovic, Jelena; Choi, Yoosu; Deweerth, Stephen P.; Glezer, Ari; Allen, Mark G., "Microfabication Technologies for a Coupled Three-Dimensional Microelectrode, Microfluidic Array," J. Micromech. Microeng. 17, Jan. 2007, pp. 163-171.

Reynaud, J.C.; Martini F.; Chatel, C.; Buclin, M.; Raggenbass, M.; Puizillout, J.J., "A New Interface Chamber for the Study of Mammalian Nervous Tissue Slices," Journal of Neuroscience Methods 58, Jan. 1995, pp. 203-208.

Aschner, Michael, "Neuron-Astrocyte Interactions: Implications for Cellular Energetics and Antioxidant Levels," NeuroToxicology 21(6), Dec. 2000, pp. 1101-1107.

Fawcett, James W.; Barker, Roger A.; Dunnett, Stephen B., "Dopaminergic Neuronal Survival and the Effects of bFGF in Explant, Three Dimensional and Monolayer Cultures of Embryonic Rat Ventral Mesencephalon," Experimental Brain Research, Vo. 106, No. 2, Jan. 1995, 106, pp. 275-282.

Fawcett, James W.; Housden, Elizabeth; Smith-Thomas, Linda; Meyer, Ronald L., "The Growth of Axons in Three-Dimensional Astrocyte Cultures," Developmental Biology 135, Oct. 1989, pp. 449-458.

Nicoll, R.A.; Alger, B.E., "A Simple Chamber for Recording from Submerged Brain Slices," Journal of Neuroscience Methods, 4, Aug. 1981, pp. 153-156.

Palovcik, Reinhard A.; Phillips, M. Ian, "A Constant Perfusion Slice Chamber for Stable Recording During the Addition of Drugs," Journal of Neuroscience Methods, 17, Aug. 1986, pp. 129-139.

Schmeichel, Karen L.; Bissell, Mina J., "Modeling Tissue-Specific Signaling and Organ Function in Three Dimensions," Journal of Cell Science 116, Jun. 2003, pp. 2377-2388.

Zbicz, Kerry L.; Weight, Forrest F., "Transient Voltage and Calcium-Dependent Outward Currents in Hippocampal CA3 Pyramidal Neurons," Journal of Neurophysiology, vol. 53, No. 4, Apr. 1985, pp. 1038-1058.

Wereley, S.T.; Meinhart, C.D., "Micron-Resolution Particle Image Velocimetry in Microscale Diagnostic Techniques," Breuer, Kenny (Ed.), Dec. 2005, Springer, XII, pp. 1-67.

Brewer, G.J.; Fogleman, C.N.; Vukasinovic, J., Glezer, A.; Deweerth, S.P.; Rowe, L.E.; Frazier, A.B., "Fluidics Improve Survival on a Microscaffold for 3D Culture of Neuronal Networks," The Oct. 2006 Annual Fall Meeting of the Biomedical Engineering Society, Chicago, IL. This was a Poster at the event. Poster not provided.

Rambani, K.; Vukasinovic, J.; Glezer, A.; Potter, S.M., "Maintaining Viable Thick Cortical Slices by Perfusion of Nutrient Medium," Society for Neuroscience Meeting, Oct. 2006, p. 1.

Shi, Wei-Xing; Bunney, Benjamin S., "A Small Volume Chamber for Electrical Recording from Submerged Brain Slices and a Pulse-free Medium Supply System Using a Peristalic Pump," Elservier Science Publishers (Biomedical Division), Dec. 1990, pp. 235-240.

Richards, C.D.; Tegg, W.J.B., "A Superfusion Chamber Suitable for Maintaining Mammalian Brian Tissue Slices for Electrical Recording," Proceedings of the B.P.S., Jan. 1977, p. 526.

Papra, A. et al., "Microfluidic Networks Made of Poly(dimethylsiloxane), Si, and Au Coated with Polyethylene Glycol for Patterning Proteins onto Surfaces," Langmuir (vol. 17) Jun. 2001, pp. 4090-4095.

Vukasinovic, J. et al., "A Microfluidic Perfusion Chamber for Neuronal Cultures," Proceedings of 2006 ASME Summer Bioengineering Conference, Jun. 2006, pp. 1-2.

Cullen, D. K. et al., "High Cell Density Three-Dimensional Neural Co-Cultures Require Continuous Medium Perfusion for Survival," Proceedings of 28th Annual International Conference IEEE Engineering Medicine and Biology Society, Aug. 2006, pp. 636-639.

Cullen, D. K. et al., "," Proceedings of Society for Neuroscience 36th Annual Meeting, Oct. 2006, (2 pages).

Tsacopoulos, M. et al., "Metabolic Couping Between Glia and Neurons," Journal of Neuroscience 16, Feb. 1, 1996, pp. 877-885.

Dertinger, S. K. W. et al., "Generation of Gradients Having Complex Shapes Using Microfludic Networks," Analytical Chemistry, vol. 73, No. ??, Feb. 2001, pp. 1240-1246.

Baier H. et al., "Axon Guidance by Gradients of a Target-Derived Component," Science, vol. 255, Jan. 24, 1992, pp. 472-475.

* cited by examiner

CENTIMETER-SCALE, INTEGRATED DIAGNOSTICS INCUBATOR FOR BIOLOGICAL CULTURING

CROSS REFERENCE TO RELATED APPLICATIONS

This application claims priority to U.S. provisional application entitled "LOW-COST, CENTIMETER-SCALE, INTEGRATED DIAGNOSTICS INCUBATOR FOR BIOLOGICAL CULTURING" having Ser. No. 60/697,437, filed Jul. 8, 2005.

STATEMENT REGARDING FEDERALLY SPONSORED RESEARCH OR DEVELOPMENT

This invention was made with government support under agreement I ROI EB00786-01 awarded by the National Science Foundation. The Government has certain rights in the invention.

BACKGROUND

The present invention relates generally to portable, diagnostics, pocket-size incubators with integrated perfusion, and more particularly, to a biocompatible, disposable, centimeter-scale, incubator workstation 10 for in situ monitoring, handling and scientific studies of biological cultures in the field and within major laboratories.

Currently, the handling of biological samples intended for experimentation and diagnostic analysis is often limited by the need to carefully manage the conditions of perfusion and incubation, and to quickly return the samples to a controlled environment, especially in field situations. In many cases, necessary manipulation of samples for analytical purposes can result in unwanted contamination, lost time and considerable costs associated with repeat experiments.

Conventional incubators are relatively large devices, having a size that is comparable to a small bar refrigerator. Typically, static cultures are formed on Petri dishes and then placed in the incubator on shelves. While the incubator may typically have temperature, humidity and gas control, there is generally no provision for optically inspecting the cultures without opening the incubator and removing the Petri dish from the incubator. This exposes the culture to possible contamination, and may cause other problems relating to culture growth. Hence, it would be desirable to have an improved centimeter-scale, diagnostics incubator with integrated perfusion that may be used to culture biological samples with the better control of the cellular micro-environment. It would also be desirable to have a centimeter-scale, integrated diagnostics incubator that permits in-situ optical inspection of cultures within the incubator.

Experiments involving physiologically faithful, thick, three-dimensional (3-D) in-vitro cultures are time constrained as the tissue decays metabolically in the absence of functional vasculature and perfusion, often well before the relevant studies have been completed. Thus, it would be desirable to a have a centimeter scale diagnostic incubator with integrated perfusion that prevents high-density cultures from decaying metabolically by actively controlling the nutrient medium exchange rate and enabling the forced convection, intercellular mass transport to overcome diffusion limits in nutrient and gas delivery through the culture.

Since high-density cultures require many cells it would be desirable that the size of the cell culture chamber be as small as possible to reduce expenditures and enable high-plating densities with the low number of cells. It would be desirable that the centimeter-scale diagnostics incubator has small overall dimensions that would facilitate the control of the cellular microenvironment and provide the shortest possible response time to the physical changes and chemical stimuli. It would also be desirable to have a centimeter-scale, integrated diagnostics incubator that is portable and may be used in the field. Ultimately, it would also be desirable to have a centimeter-scale, integrated diagnostics incubator of a modular design to address different demands.

While 2-D culturing constitutes a standard practice for many fundamental studies, researchers are increasingly implementing the 3-D cell culture systems because they are biologically more realistic in capturing the in-vivo condition than their 2-D correlates. The three-dimensionality enables scientists to investigate cellular behavior in a more physiologically relevant state, while preserving the primary advantages of traditional in vitro systems, such as the control of cellular environment, accessibility for imaging, and elimination of systemic effects. Cells cultured in a 3-D environment are found to better represent the in vivo cellular behavior than cells cultured in monolayers. This was shown for different kinds of cell lines, e.g. for fibroblasts cells by Grinnell F. in 2000 Trends Cell Biol 10:362-365; for breast cells, e.g., Wang F. et al. in 1998 Proc Natl Acad Sci USA 95:14821-14826; for osteoblastic cells, by Granet C. et al. in 1998 Med Biol Eng Comput 36:513-519; and, neural cells by Fawcett J. W. et al. in 1989 Dev Biol 135:449-458, or Fawcett J. W. et al. in 1995 Exp Brain Res 106:275-282.

The way cells interact with each other and their microenvironment is fundamentally different in 3-D and 2-D cultures, see for example Schmeichel K. L. et al. in 2003, J Cell Sci 11:2377-2388. In many cases these interactions are reduced or negligible in 2-D cultures. This necessitated the development of neural cell culture models to support high, 3-D cellular densities with cells evenly distributed throughout the full thickness of the matrix. The extracellular matrix material supports the cells in a 3-D setting, and, enhances cell-to-cell and cell-to-matrix interactions, e.g., O'Connor S. M. et al. in 2001 Neurosci Lett 304:189-193; Woerly S. et al. in 1996 Neurosci Lett 205:197-201. However, these cultures have relied on passive diffusion for nutrient delivery and removal of toxic waste products necessitating the use of cell densities much lower than those found in the brain for example. Therefore, diffusion limited mass transport in nutrient delivery prevented the development of more in vivo resembling 3-D neural cell culture models having high cellular density ($\geq 10^4$ cells/mm$^3$) and uniform cell distribution throughout culture thickness (>500 μm).

Growing demands for long-term incubation of physiologically faithful, three-dimensional (3-D) neuronal and other cultures during extended physiological studies require efficient perfusion platforms with functional vasculatures that mimic the in vivo condition in a thermally regulated environment. While expensive, relatively small, incubation baths with thermostatically controlled water jackets and capillary action perfusion are available commercially, to date, they remain incompatible with the microfabrication processes with their use confined to specific experimental conditions associated with the limits of capillary action perfusion. Representative incubation baths with passive perfusion are disclosed by Haas H. L. et al. in 1979 J Neurosci Meth 1:323-325, and, Zbicz K. L. et al. in 1985 J Neurophysiol 53:1038-1058.

The widespread use of 3-D neural cultures in medical research, however, is often hindered by low water solubility of oxygen, limited diffusion of media and oxygen through the tissue, and poor waste removal. Once the slices are being harvested, the utility of experiments is restricted by the quality of tissue perfusion, as the success of electrophysiological studies, for example, depends on long term slice viability to take reliable recordings.

There are generally two kinds of perfusion chambers that are being used to extend the viability of acute tissue slices in vitro based on constant circulation of the culture medium by passively augmenting the supply of media and oxygen. In the first kind, the tissue is submersed in the bathing solution and perfused using oxygenated media as discussed by Richards C. D. et al. in 1977 Br J Pharmacol 59:526P; Nicoll R. A. et al. in 1981 J Neurosci Meth 4:153-156; Palovcik R. A. et al. in 1986 J Neurosci Meth 17:129-139; Shi W. X. et al. in 1990 J Neurosci Meth 35:235-240, for example. In the second kind, the tissue rests on a mesh at the interface between the open channel flow of perfusate, underneath the mesh holding the tissue, and oxygenated and humidified atmosphere above the mesh. Representative chambers are described by Li C. L. et al. in 1957 J Physiol-London 139:178-190; Reynaud J. C. et al. in 1995 J Neurosci Meth. 58:203-208; Krimer L. S et al. in 1997 J Neurosci Meth 75:55-58.

Both approaches have practical benefits and shortcomings. The principal advantage of the submerged tissue incubation is faster diffusion of the bathing solution into the slice than in interface type chambers where only one side of the tissue is exposed to the media, not both. Although intuitively tissue would seem to have better oxygenation lying at the interface than being submerged, due to limited water solubility of oxygen in the latter, Croning M. D. R. et al. in 1998 J Neurosci Meth 81:103-11 found that the degree of disruption of ionic homeostatis by anoxia in rat hippocampal slices was greater when they were maintained at the interface. This could be attributed to the discontinuities in the flow of media associated with the surface tension effects at the gas-liquid interface. In addition to being simpler to design, submerged chambers provide more constant environment with less perturbations in fluid flow, purging of bubbles, and, draining, and, permit rapid exchanges of the bathing medium. Hence it appears that better perfusion fixation, in preventing both the starvation and anoxia during the process of observation, can be achieved in submerged chambers. Still, a major drawback in submerging the tissue below the liquid surface is actually keeping it submerged, because it will float unless it is properly attached to the perfusing substrate or restrained otherwise. In addition, localized injection of drugs is virtually impossible to administer with the current designs.

The dominant mode of mass transport in these scarcely used chambers remains diffusion and/or capillary action to passively augment the supply of media and oxygen to the tissue that eventually runs down metabolically. However, to meet and exceed the metabolic requirements for nutrient delivery and catabolic waste removal, mass transport by pure diffusion becomes insufficient and demands a convective enhancement for an adequate, dynamic, long-term control of the culture condition.

BRIEF DESCRIPTION OF THE DRAWINGS

The various features, functionalities and practical advantages of the present invention may be more readily understood with reference to the following detailed description taken in conjunction with the accompanying drawings, wherein like reference numerals designate like structural elements, and in which.

DETAILED DESCRIPTION

Figure 1:
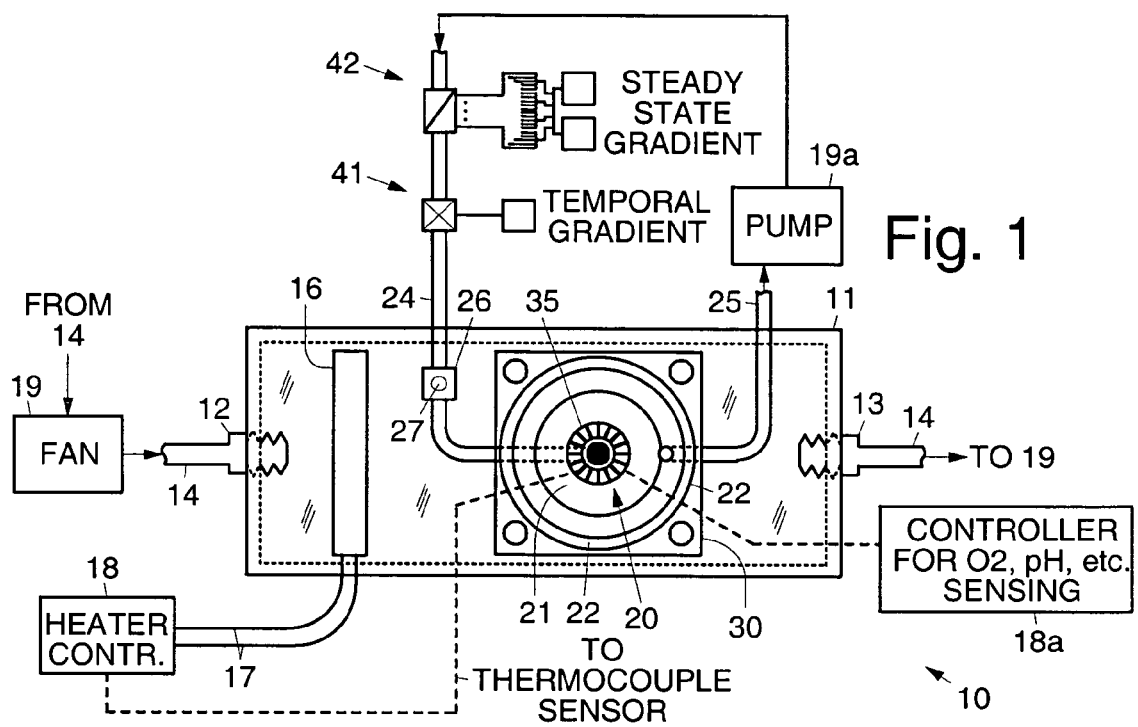
FIG. 1 is a top view of an exemplary centimeter-scale, diagnostics incubator with integrated perfusion.

To overcome problems associated with conventional incubator technologies, and referring to the drawing figures, disclosed is a biocompatible, centimeter-scale, diagnostics incubator 10 having an integrated microfluidic perfusion chamber 30 which allows simultaneous culturing and experiments on a bench top or a microscope stand, with full control of the environmental conditions, fluidic, optical, and, electrical accessibility. By way of illustration, FIG. 1 shows an exemplary centimeter-scale, integrated diagnostics incubator 10 comprising an exemplary integrated perfusion chamber 30.

As is shown in FIG. 1, an exemplary reduced-to-practice centimeter-scale, integrated diagnostics incubator 10, or mini-incubator 10, comprises a biocompatible, polystyrene, heated enclosure 11 with exemplary outside dimensions of 5.1×2.5×1.8 cm (L×W×D). The enclosure 11 has a removable top cover that facilitates the integration and packaging. Owing to the clarity of the polystyrene material, all surfaces of the enclosure 11 are optically transparent and enable visual inspection.

The incubator 10 houses a biocompatible polydimethylsiloxane (PDMS), for example, perfusion chamber 30 with a centrally placed cell culture life support perfusion chamber 20, a semi-permeable membrane aerator 21, a miniature, thin flexible heater 16 that maintains a desired temperature within the incubator 10 or heated enclosure 11, an in-line venting bubble trap 26 and a membrane aerator 27 for injected nutrient medium, thermocouple sensors connected to a temperature controller 18, and; pertinent gas 12, 13 and fluidic interfaces 24, 25. The optically clear incubator enclosure 11 and a semi-permeable membrane aerator 21 permit optical examination or observation of a culture growing within the culture chamber 20. Imaging accessible, semi-permeable membrane 21 (aerator 21 or oxygenator 21), located on the top of the perfusion chamber 30, ensures sufficient gas delivery and provides sterile, moist microenvironment of appropriate acidity.

On the sides of the heated enclosure 11 there are separate gas connectors that enable the appropriate gas mixture to enter and leave the incubator 10 at a desired volume flow rate. A forced convection flow of gases, such as 95%/5% oxygen/carbon dioxide mixture for example, enters tough gas inlet 12 and outlet port 13. The gas inlet 12 and outlet 13 ports are coupled to gas lines 14 that lead to a separate miniature box (not shown) that houses a fan 19 and contains prescribed gas mixture via shut-off valve connection to a gas tank. A fan 19 can be a pair of miniature blowers with the overall dimensions of 4 cm×4 cm×4 cm used in electronics cooling (Thermaltake A1899, for example). Blowers force the appropriate gas mixture through the gas lines 14 and optically clear enclosure 11 and allow external control of the fan speed to provide an optimal gas rate at a minimal noise level.

There are two fluidic interfaces for the nutrient medium, for example. They are associated with continuous infusion of the nutrients into the perfusion chamber 30 and withdrawal of used media and metabolic waste products at the same rate. All fluidic components (perfusion chamber 30, aerators, fittings and tubes) are steam autoclavable (re-usable) with stiff microbore tubes fabricated in an inert (Teflon FEP) material that minimizes the problems associated with bio-fouling (non-specific protein adhesion along the inner walls). Fluidic inlet and outlet ports 24, 25 are coupled to the infusion and withdrawal side of the syringe pump moving block respectively. An exemplary syringe pump 19a with opposing syringes on a single drive may be a KdScientific pump model KDS210, for example. The pump mode of operation pertinent to the particular cell feeding schedule is externally controlled and can be a continuous infusion and withdrawal; programmable, time-periodic or aperiodic infusion and withdrawal; or, push/pull; with or without the re-use of spent perfusate. In either mode, while one syringe infuses the media, the other syringe withdraws the perfusate at the same rate so that the pressure within the cell culture chamber 20 remains at or near the atmospheric level. This particular mode protects the cultures from prohibitively high pressures otherwise associated with the return flow from the chamber. In a portable design, syringe pump 19a can be replaced with a pair of miniature piezoelectric pumps that can be battery operated (e.g. only 0.15 W of power for Clark DTI-200-12P measuring 4-5 cm) and fluid delivery rates manipulated by varying the amplitude or the frequency, or both, of the power supplied using an inexpensive custom built function generator based on the operational amplifier circuits, for example.

Unlike commercially available (Zbicz- or Haas-type) perfusion chambers, disclosed manufacturable, cost efficient, disposable or autoclavable, microvascular perfusion chambers 30 can be easily configured to meet specific demands while exceeding the available exchange rates of commercial devices by a few orders of magnitude. Fluidic functionality of the perfusion chamber 30 enables the culturing of thicker tissue slices and engineered 3-D culture models that better represent the in-vivo condition via forced convection intercellular mass transport that is not feasible in commercially available interface or submerged-type perfusion chambers. A simple fabrication methodology based on elastomeric polymer molding allows the integration of microfluidic and MEMS components (not shown) into the perfusion chamber 30, such as micropumps, valves, mixers, microinjectors, cellular manipulators or multielectrode arrays, for example. It also facilitates the interfacing of perfusion chambers 30 and incubators 10 and enables the integration of a number of plug-in functionalities into the mini-incubator 10 tailored to specific use in a short turn-around time.

The disclosed fluidic design also enables the introduction of externally controlled temporally varying 41, or, spatially varying, temporally invariant concentration gradients 42 of injected agents into the culture chamber 20, with fluidic infrastructure and control located outside of the incubator enclosure 11. Owing to the flexibility of the perfusion system, the nature of cell feedings can be radically changed. For example, a programmable time-periodic injection of nutrients can be employed, followed by times where perfusion chamber 30 acts as a static control; the media could also be cycled in and out of the chamber 30 in some periodic or aperiodic fashion to break the temporal invariance of spatial gradients; or, the ratio of fresh to used media can be varied to increase the amount of cytokines (neurotrophins, for example) if the need arises. The fluidic system may be easily adapted to address and individually control multiple culture chambers 20 or perfusion chambers 30.

Drugs can be discretely applied to specific regions using separately addressable fluidic inputs, interfaced outside the incubator 10 and introduced into the perfusion chamber 30 through the inlet port 33 (FIG. 5) or a plurality of inlet ports 33 (not shown), as could other substances. This makes the centimeter-scale incubator 10 ideal for time-dependent pharmacological studies at dynamically controlled exchange rates directly on a microscope stand, for example. Extra- and intercellular ion concentration can be accurately controlled and easily altered. By collecting the spent perfusate, substances released during stimulation can be easily analyzed. Collected perfusate can be mixed with the fresh medium and re-used, particularly at high exchange rates and cell densities when neurotrophins may be depleting.

Figure 7:
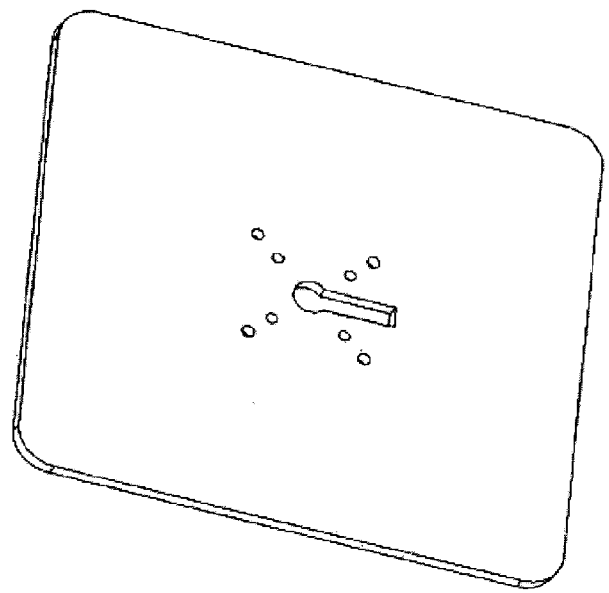
FIG. 7 illustrates an exemplary microscope stage insert plate that can be used to attach the centimeter scale incubator with an integrated perfusion chamber onto a microscope stage.

The centimeter-scale incubator 10 with its integrated perfusion chamber 30 permits simultaneous studies of cell culture parameters using optical diagnostics. For this purpose, a particular microscope stage insert may be used. The incubator 10 or perfusion chamber 30 connects directly to the microscope stage insert plate by way of 4 screws and nuts that pass through four through-holes located on the body 31 (FIG. 2) of the perfusion chamber 30 and centimeter-scale incubator 10. This enables in situ cell culture viability studies and immunocytochemistry, for example, below the microscope objective. An exemplary microscope stage insert, shown in FIG. 7, was built using stereolithography.

A heating element 16, such as a miniature (2 cm×2.5 cm) resistive foil heater 16 (Minco HK5291, for example) is disposed within the enclosure 11 and has the lead wires 17 extending outside of the enclosure 11 to a temperature controller 18 coupled to a DC switching relay and a DC power supply that can be replaced with a battery for portability. Typical power requirements for the heating element 16 integrated within the incubator 10 are at the order of just 1 W. To enable tissue preservation, the resistive heating element 16, can be replaced with a thermoelectric pump, for example, to maintain the temperature below the ambient.

Although not shown, additional sensors and controllers including but not limited to glucose consumption, pH or dissolved $O_2$ sensing and control 18a can be easily integrated into the perfusion chamber 30 and the enclosure 11 depending on particular demand. The modular design allows integration of all or some of the above mentioned elements and enables the packaging of a larger number of perfusion chambers 30 into a common, environmentally regulated enclosure 11. Higher number of independently controlled perfusion chambers 30, within an enclosure 11 enables high throughput processing of a number of cultures onboard a single, disposable platform.

Figure 2:
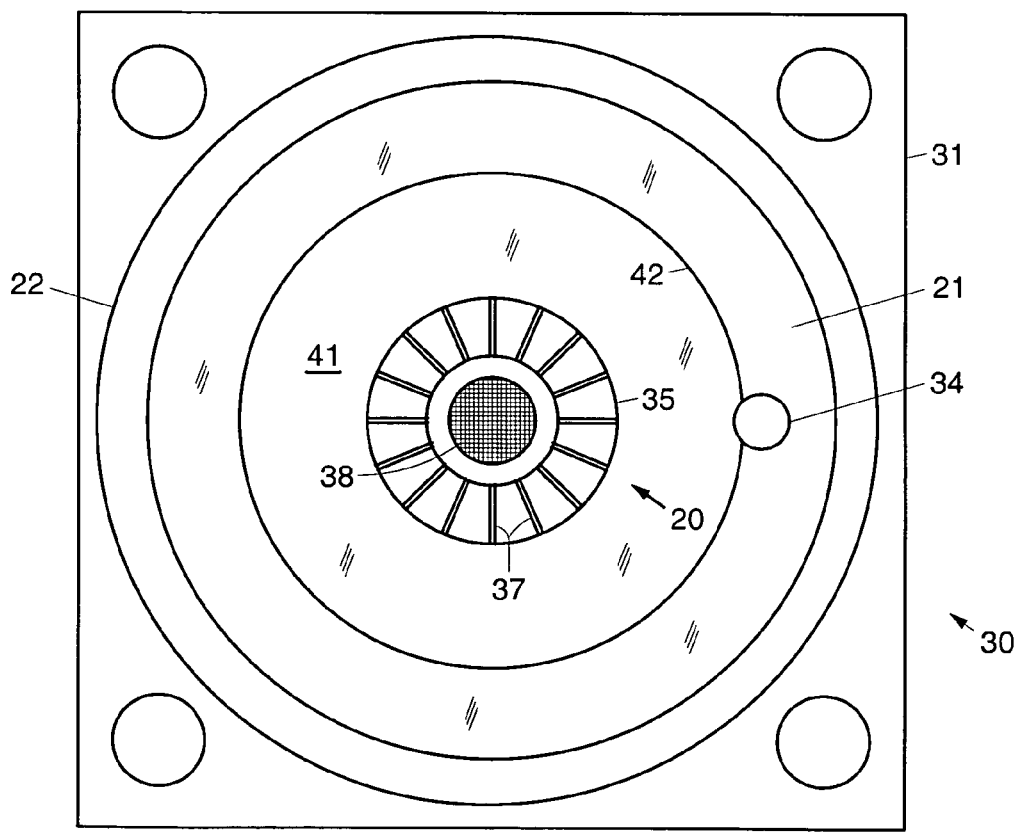
FIG. 2 is a top view of an exemplary microfluidic perfusion chamber that may be used in the diagnostics incubator and that comprises a culture chamber with fluidic ports and attached semi-permeable membrane that encapsulates the structure.
Figure 3:
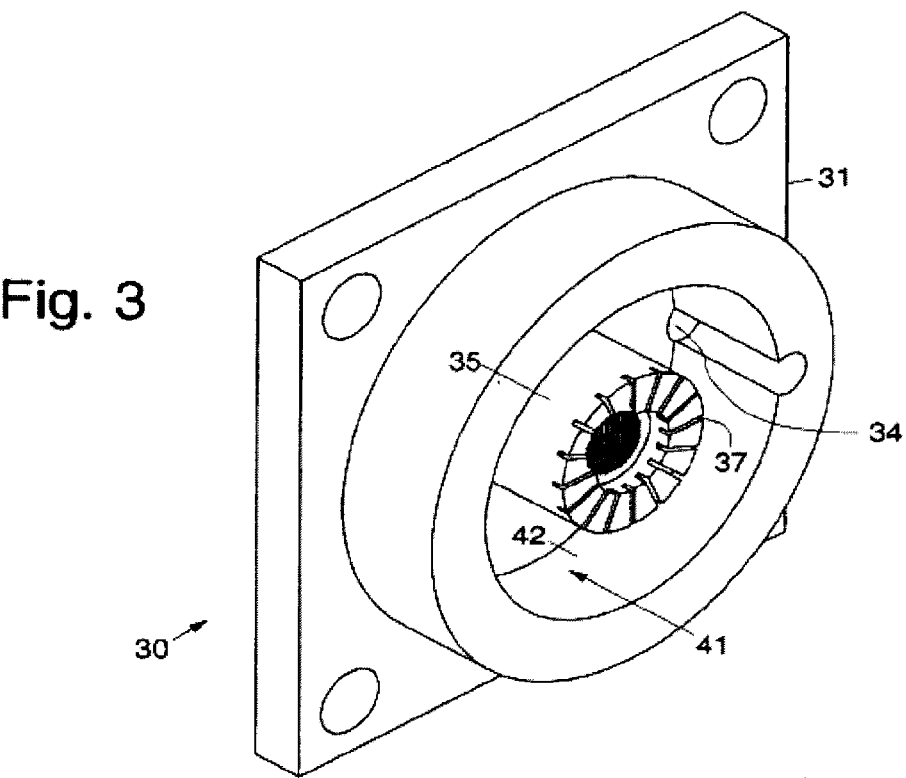
FIGS. 3 and 4 illustrate three-dimensional views of the exemplary perfusion chamber.
Figure 4:
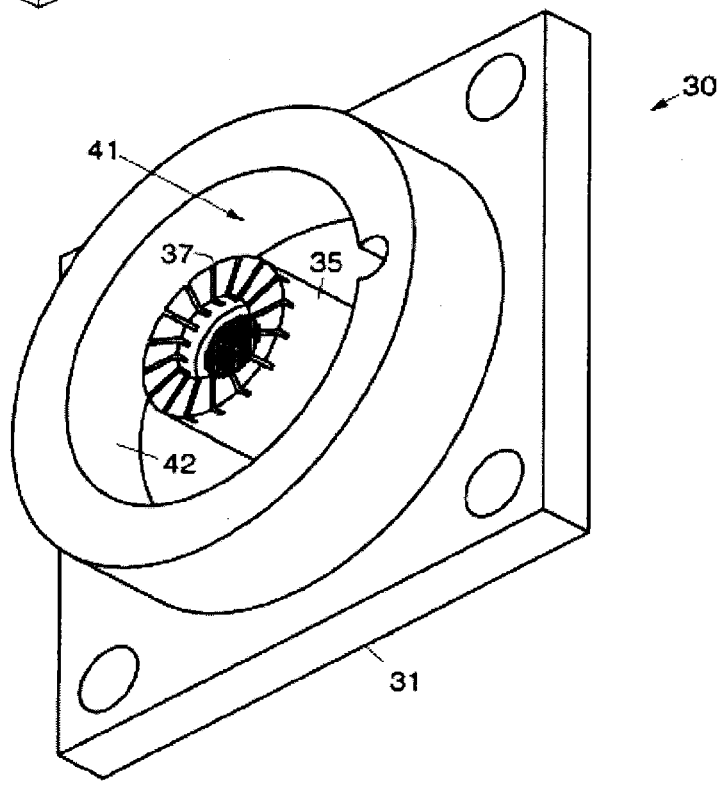
Figure 5:
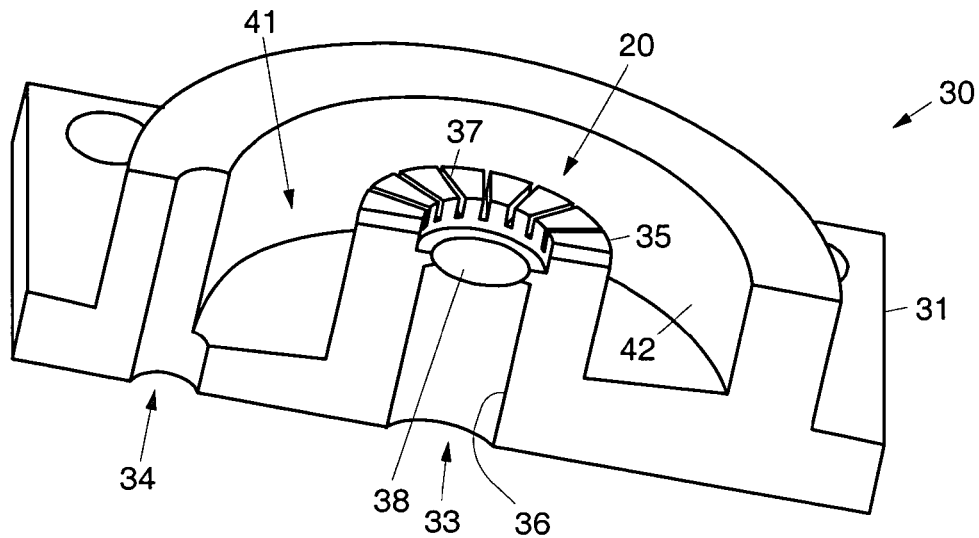
FIG. 5 is a cross-sectional view of the exemplary perfused culture chamber with integrated microfluidics.
Figure 6:
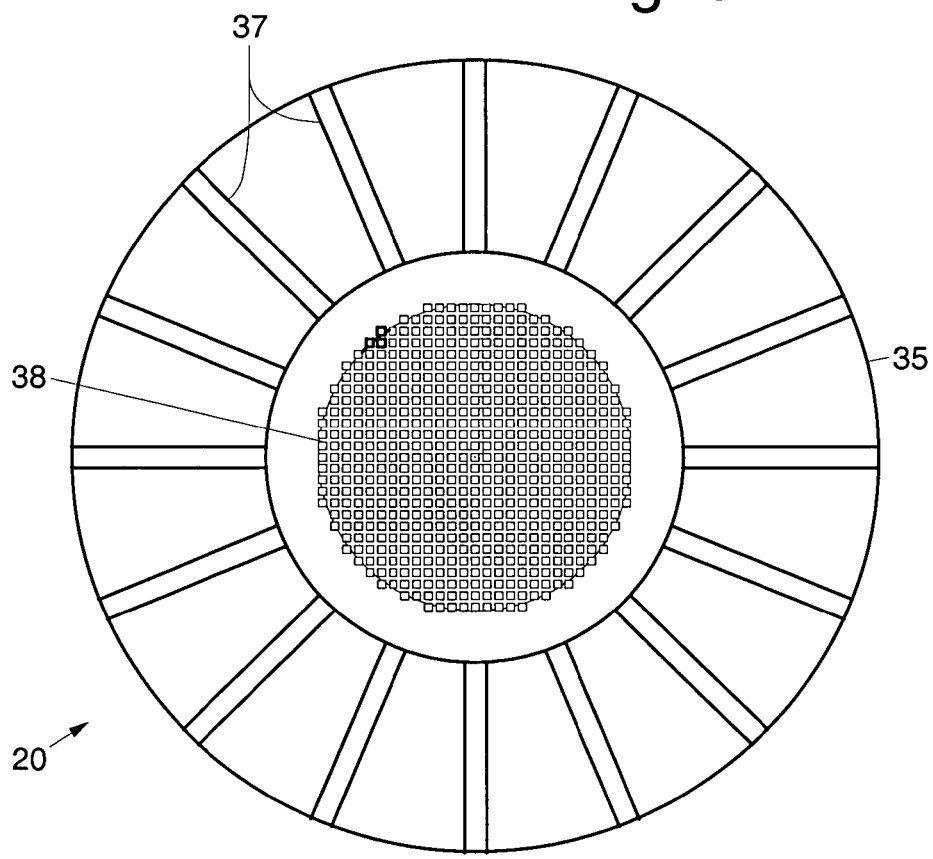
FIG. 6 is a top view showing details of a cell culture life support chamber centrally integrated within the perfusion platform.

FIG. 2 shows top view of the exemplary microfluidic perfusion chamber 30 and a cell culture life support chamber 20. FIGS. 3 and 4 illustrate three-dimensional views of the perfusion chamber 30. FIG. 5 is a cross-sectional view of the perfusion chamber 30 and a cell culture chamber 20. FIG. 6 illustrates a top view showing details of the culture chamber 20 centrally formed in the perfusion chamber 30.

As is shown in FIG. 2, the exemplary perfusion chamber 30 comprises a body 31, which may be made of polydimethylsiloxane (PDMS), for example, and a semi-permeable membrane holder 22 that encapsulates the perfusion chamber 30. A central opening is formed in the body 31 that defines the inlet port 33 (FIG. 5) with the exit port 34 embedded into the bottom of the return flow (consisting of the used media and catabolites) collecting pool 41. The return flow collecting pool 41 is formed in the body 31 between cylindrical enclosures 35, 42. The fluidic inlet and outlet ports 33, 34 are coupled to a syringe pump 19a via inlet and outlet tubing 24, 25 (shown in FIG. 1). An optically clear membrane 21, such as a hydrophobic, fluorinated-polyethylene-propylene (FEP) membrane 21, see for example, Potter S. M. et al. in 2001 J Neurosci Meth 110: 17-24, is attached to the top of the body 31 via miniature Teflon holder 22 with O-rings to seal the chamber 30 (see FIG. 2). The transparent membrane 21 contacts the top surfaces of the perfusion chamber 30 and culture chamber 20 while O-rings seal the device exterior wall 42 of the body 31, and thus the entire perfusion chamber 30. The FEP membrane 21 is impermeable to the media but permeable to gases necessary for cellular metabolism. The transparent membrane 21 secured with a Teflon holder 22 permits optical examination or observation of the tissue within the culture chamber 20. Such observation is not possible using conventional, large-scale incubators. Typically, culturing takes place in the incubator and tissue has to be taken from the refrigerator size incubator to be observed and analyzed under a microscope.

The body 31, as shown in FIGS. 3 and 4, of the perfusion chamber 30 is configured to have a centrally located cylindrical, cell culture life support chamber 20, an outer inclined, collecting pool 41, and, fluidic inlet and outlet ports 33, 34 shown in FIG. 5. The culture chamber 20 as schematically shown in FIG. 6 is an actively controlled incubation bath bounded by the perfusing substrate 38 that supports the tissue, located at the bottom of the culture chamber 20, cylindrical sidewall 35 that confine the culture to the area immediately above the substrate 38, and the optically clear semi-permeable membrane 21 attached to the top of the perfusion chamber 30 and held by the Teflon holder 22. A smooth, continuous, circulation of the media and analytes is achieved by using a simultaneous push-pull pumping system in which the output exactly balances the input, that is, the culture feedings are in mass equilibrium with the amount of retrieved perfusate. The level of bathing medium within the culture chamber 20 is controlled by the suction side of a syringe pump 19a. Nutrients enter the perfusion chamber 30 through the inlet port 33 before being distributed through the perfusion substrate 38, and further, throughout the volume of the culture chamber 20 (see FIG. 5). Used media and metabolic waste products are withdrawn from the cultured chamber 20 through an array of microchannels 37 that are incorporated into the walls of the cylindrical PDMS enclosure 35 bounding the culture chamber 20. Retrieved perfusate is collected within the inclined pool 41, outside the culture chamber 20, before it is withdrawn through the outlet port 34. The bottom surface of the exit flow collecting pool 41 is slanted to allow the used perfusate accumulating in the pool 41 to migrate toward the outlet port 34 formed in an exterior wall 42 of the body 31. A 6° inclination, for example, of the bottom surface of the pool 41 helps in steering the used media and catabolites towards the outlet port 34.

The cylindrical sidewall 35 that surrounds the culture chamber 20 measures 3.5 mm in diameter and raises 700 µm above the perfusion substrate 38 so that the exemplary, effective volume for 3-D culturing amounts to about 7 µl. Media enters the culture chamber 20 from an array of micronozzles, normal to the perfusing substrate 38 (FIG. 6) that upholds the tissue, and exits through plurality or radial slots 37 or microchannels 37 formed within the cylindrical enclosure 35 that confines the tissue laterally. Exemplary 150 µm wide microchannels 37 are 375 µm deep and start at the elevation of 375 µm above the perfusion substrate 38. These microchannels 38 allow used cell culture media to leave the culture chamber 20. The start of the microchannels 38 at a mid-height of the cylindrical enclosure 35 enables the tissue to always be at least partly submerged. By filling the entire culture chamber 20 first, without starting the suction, one can ensure that the culture is fully submersed prior to the start of a closed-loop circulation. The radial exit flow through the microchannel array 37 peripherally located within the culturing chamber 20 is facilitated by the presence of a selectively permeable membrane 21 placed over the top of the perfusion chamber 30. While traditional perfusion platforms rely mainly on diffusion and/or capillary action, the incubator 10 disclosed herein provides an efficient control of both convective and diffusive mass transport relying on interstitial nutrient convection induced by an array of microjets issuing from micronozzles formed in the perfusing substrate 38 that upholds the tissue and peripheral extraction of the perfusate, by an array of microchannels 37, for example, located within the cylindrical enclosure 35 that laterally confines the tissue. Actively growing high density cultures are continually perfused with the fresh medium. Volumetric flow rates for neuronal-only and neuronal/astrocytic co-cultures range from 0.1-0.4 µL/min. The cell longevity is the dominant factor determining the flow rate of the supplied media. Collected perfusate can be mixed with the fresh medium and reused, particularly at high exchange rates and cell densities when neurotrophins may be depleting.

The perfusing substrate 38 may be made of gold, for example, and bonded to or otherwise sealed to the lip formed at the bottom of the culture chamber 20. An exemplary gold perfusion substrate 38 (such as PELCO® center-marked grids, 300 mesh, 1GG300, for example) measures 3 mm in diameter and contains 54 µm square openings (micronozzles) with center-to-center spacing of 85 µm. This yields 40% open area for fluid flow. Different perfusion substrates 38, of different topology and surface chemistry for example, may be used to promote cellular adhesion to the bottom of the culture chamber 20 and enable perfusion of the tissue cultured inside. Micronozzles can have sub-cellular dimensions, i.e., 5 µm for example, which is well below the size of the neural cell body (about 10 µm). Various kinds of commercially available or custom made substrates 38 having different porosity and hydraulic diameters, can be bonded to the bottom of the culture chamber 20 using a thin layer of PDMS pre-polymer. This allows manipulation of the cellular microenvironment by altering the flow conditions and cellular adhesion. A variety of biocompatible materials, other than gold, may be used as perfusion substrates 38 and to support the cells cultured within the culture chamber 20. For example, thin nylon membranes, polycarbonate, PTFE, or PLGA films and the like, may be used. In fact, in some cases selective coating of these substrates 38 promotes preferential cell growth if desired. Cell attachment may be enhanced using a variety of biocompatible coatings, depending on the exact nature of the study and the type of cells cultured within the culture chamber 20. For example, dissociated 3-D cultures are often grown in protein rich (e.g. matrigel) or polysaccharide based extracellular matrices (e.g. agarose), see for example, O'Connor S. M., et al. in 2001 Neurosci Lett 304:189-193; or, Woerly S., et al. in 1996 Neurosci Lett 205:197-201.

The perfusion chamber 30 is aerated by a hydrophobic, fluorinated-polyethylene-propylene (FEP) membrane 21 (see U.S. Pat. No. 6,521,451, for example) that is selectively permeable to gases such as oxygen, nitrogen, hydrogen and carbon dioxide and relatively impermeable to microbes, water and water vapor (less than 0.01% moisture absorption). Multiple functionalities of the FEP membrane 21 eliminate the need to equilibrate the media in an external bath, the most frequently used type of aerator (oxygenator for acute slices) used in conventional perfusion chambers, incorporate bubble traps, or to include the gas lids to direct the moist and saturated air over the culture like in interface-type (Haas) chambers. Separate buffering of the media to achieve the appropriate acidity is also deemed unnecessary. Hence, the use of this simple, yet efficient, membrane aerator 21 enables a fine control of the cellular climate without complicated, bulky components, thus allowing the fabrication of inexpensive compact devices. Other benefits of an aerator comprising an FEP membrane 21 and a membrane holder 22 include the ability to culture in a non-humidified incubator since the media does not evaporate from the culture chamber 20 thereby reducing the risks associated with the contamination in a humid environment, and, preventing the increase in osmotic strength that can be detrimental to the cultures. Optically transparent FEP membranes are also impermeable to microbes resulting in a reduction of contamination occurrences making them ideal for microscopic imaging in a sterile environment.

In all microfluidic devices the purging of bubbles becomes a difficult problem, and while commercially available perfusion chambers usually incorporate external bubble traps, the FEP membrane 21 used in the culture chamber 20 enables sterile venting of small volumes, i.e., it constitutes an efficient auto-venting bubble trap on its own. To further reduce the amount of non-dissolved gas bubbles entering the culture chamber 20 and equilibrate the fresh media before being injected into the perfusion chamber 30, an in-line bubbler/outgassing device can be inserted into the perfusion circuit by the use of a tee 26 (e.g. Qosina® 88216 polycarbonate tee having medical grade luer ends) and held inside the incubator 10.

Figure 8:
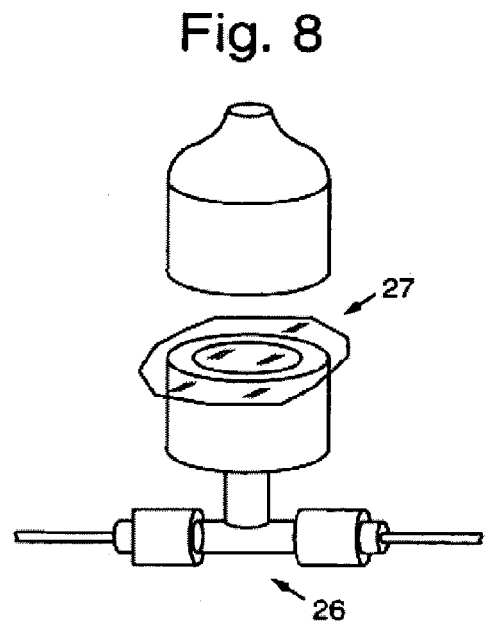
FIG. 8 illustrates an exemplary in-line auto-venting aerator and bubble trap.

To assemble the in-line bubbler/outgassing device an FEP membrane 27 is stretched over the vertical leg of the tee 26 having a male luer end, and, sealed with a finger-snap vented female luer end-cap (e.g. Qosina® 65702). This device prevents the bubbles from reaching the culture chamber 20, and ensures the media equilibrium with the gas environment inside the cm-scale incubator 10. To ensure that the media is buffered and equilibrated before entering the culture chamber 20 at high exchange rates, a larger surface area for the in-line gas exchange can be obtained alternatively. For example, an off-the-shelf filter holder (such as 13 mm Swinnex filter holder, Millipore, Billerica, Mass.) may sandwich a 12.7 μm thick hydrophobic film (Teflon® FEP film, Dupont, Circleville, Ohio) and seal it with an O-ring between the holder top- and bottom piece. This filter holder with a sandwiched FEP membrane 27, as is illustrated in FIG. 8, has a male luer-like slip that is received by a tee having a vertical female luer leg (e.g. Qosina® 80061 polycarbonate tee). When the inlet to the filter is kept in the upright position, the membrane aerator 27 helps the venting of perfusing lines thus eliminating the need for a bubble trap. This also enables a smooth circulation of the bathing medium using a syringe—rather than a peristaltic pump, as peristaltic pumps generally induce more fluctuations in nutrient delivery.

The presence of the FEP membrane 21 on the top of the culture ensures that the plethora of gas is provided from the top as is from the bottom via perfusing medium. In addition, the PDMS material used in fabricating the chamber 30 is found to be highly permeable to oxygen and carbon dioxide so that the cellular exposure to the gases is, in fact, enhanced from all exposed sides of the tissue. Hence, unlike in interface-type chambers where sufficient gas exchange is hindered by surface tension induced flow perturbations, the perfusion chamber 30 exposes both sides of the tissue to relevant gases while keeping the tissue submerged. Compared to Zbicz-type chambers where submerged tissue may suffer from anoxia due to limited water solubility of oxygen for example, in culture chamber 20 one side of the tissue is fully exposed to the gases above the FEP membrane 21, with the other side convectively bathed in equilibrated nutrient medium at high exchange rates. This enhances the thickness of slices that can be investigated in vitro compared to conventional chambers.

All components of the PDMS perfusion chamber 30 and those of relevant fluidics hardware are reusable and steam autoclavable, although the low cost of fabrication allows it to be a disposable device. The inlet and outlet fluidic connections are removable, i.e. they can be easily pushed in or disconnected from the perfusion chamber 30, which facilitates the rinsing of tubes and the perfusion chamber 30 prior to steam autoclaving them. The inlet and outlet ports 33, 34 are designed to accept standard 3/32" and 1/16" barbed, nylon adapters with 10-32 male threaded, receiving ports, respectively. These adapters can be either straight-through, for vertical tube connection, or elbow-like, to connect the tubes at a side. The adapter type depends on the spatial constraints during imaging on either upright or inverted microscopes with episcopic illumination source, such as epifluorescence. An insert plate can be custom made to match a particular microscope stage, see exemplary insert plate in FIG. 7, thus allowing perfusion experiments, injection of drugs, stimuli, cytokines and other reagents to be introduced during imaging. A receiving tefzel, 10-32 female-to-luer adapters connect to polypropylene LuerTight fittings (Upchurch Scientific). These quick-disconnect fittings conform to medical luer taper configurations with simple connection to luer lock syringes. Exemplary fittings accept 1/16" OD semi-rigid fluoropolymer tubing such as the inert, Teflon FEP, transparent tubes with 100 to 500 μm microbores. If soft tubing is to be used, then the fittings are less bulky with barbed chamber-to-tube connectors, and, luer-to-barb adapters to connect tubes to syringes. Barbed fittings require larger bore tubes, thus increasing the amount of dead volume in the system, and when the amounts of used reagents become important, the use of harder tubes is definitely warranted. While the interfacing of the perfusion chamber 30 with the cm-scale integrated, diagnostics incubator 10 is fairly straightforward, hard tubing facilitates the placement of the incubator 10 onto a microscope stage with no interruptions to the flow whatsoever.

Velocity Measurements

The perfusion chamber 30 and incubator 10 exposes the cells cultured in a culture chamber 20 to a continuous, direct flow of media through an array of micronozzles formed by the orifice plate 38 and creates 3-D, convectively biased circulation towards the perimeter of the culture chamber 20 where perfusate leaves through an array of microchannels 37. The flow under consideration is studied experimentally using microscopic particle image velocimetry, μ-PIV (see for example, Wereley S. T. et al., Micron resolution particle image velocimetry, in Diagnostic techniques in microfluidics, Editor K. Breuer, New York, Springer Verlag, 2004) to obtain reliable and reproducible two-dimensional velocity fields in the planes normal to the optical axis with high accuracy and relatively high spatial resolution. PIV is a well accepted, non-intrusive measurement technique where the fluid velocity is measured by recording the displacement of small tracer particles added to the fluid under the assumption that the particle density is identical or commensurate to that of the surrounding fluid, and its size small enough to follow the flow faithfully without influencing the flow itself (low Stokes number). Microscopic PIV is a modification of a standard PIV technique to enable spatially resolved measurements of instantaneous velocity distributions in sub-millimeter scale flow domains and allow detection of micron-scale spatial structures within the flow.

In the present experiments velocity resolution is within 5% of the microjet ejection velocity. Velocity distributions in the x-y planes, parallel to the perufsing substrate 38, and normal to the axes of microjets emanating from about 570 square micronozzles formed at the perfusing substrate 38, are shown in FIGS. 9a-l with the elevation, z, measured from perfusing substrate. The field of view measures 450×457 μm and covers the central part of the pefusing substrate 38, FIG. 9a, with an array of about 6×6 nozzles in focus. The nominal volume flow rate through the perfusion chamber is 5 μl/min with micro-jet ejection velocity of 30 μm/s and a nozzle based Reynolds number of 0.002. A small culturing volume (about 7 μl) allows rapid exchange of perfusate (about 40 exchanges per hour for the present experiments) facilitates control, and reduces the amount of spent media.

The dynamics of induced flow within the culture chamber 20 varies with elevation. Spatial structure alters from discrete microjets interacting with the stagnant fluid upon their discharge from the micronozzles, jet-to-jet interactions associated with their broadening as they decelerate downstream from the nozzles and exchange momentum with the relatively quiescent medium within the culture chamber 20, to stagnation/impingment flow with concomitant development of decelerating wall jets (along the FEP membrane 21 or a target surface) subject to biased discharge through peripherally located microchannel exits 37.

Figure 9A:
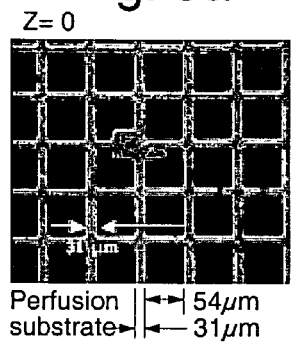
FIGS. 9a-l show particle image velocimetry measurements of the induced flow within the culture chamber at different elevations parallel to the perfusing substrate.
Figure 9B:
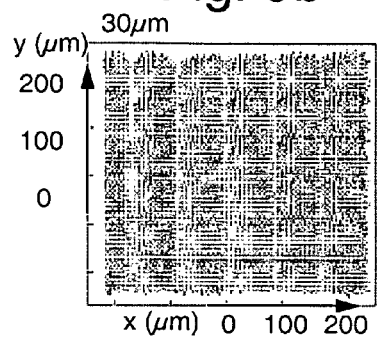
Figure 9C:
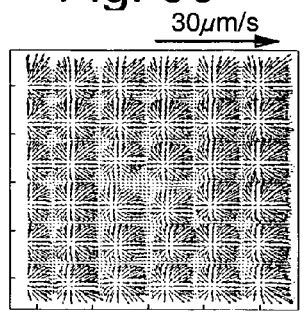
Figure 9D:
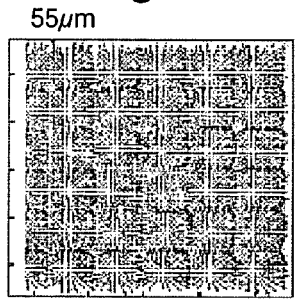

Close to the perfusing substrate 38 shown in FIG. 9a, flow is characterized by semi-confined, submerged, laminar impinging microjets issuing from an array of about 570 micronozzles (formed at the perfusing substrate 38) at moderate target-to-nozzle spacing. Upon their discharge from the nozzles, normal to the perfusing substrate 38, microjets interact with the stagnant medium within the culture chamber 20 as demonstrated in the sequence of images in FIGS. 9b-d normal to the jet axe. This shear driven interaction enables them to spread out. Measured spanwise velocity distributions reveal that the free boundary of microjets broaden with elevation, which is manifested by higher magnitudes of the induced velocity in the x-y planes, parallel to the perfusing substrate 38, as jets decelerate streamwise (along their axe) and accelerate in transverse planes. Momentum exchange between the jets and the stagnant medium causes this broadening with concomitant reduction in jet axial (streamwise) velocity. Before the jet interactions begin flow symmetry is determined by the number of microjets, with no apparent preferential direction as is shown in FIG. 9d.

Figure 9E:
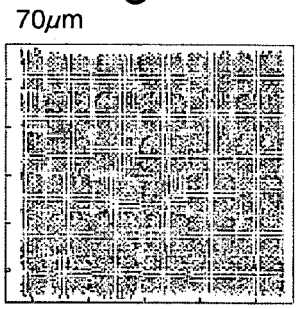
Figure 9F:
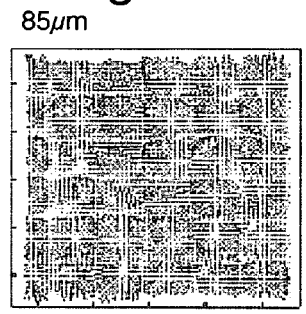
Figure 9G:
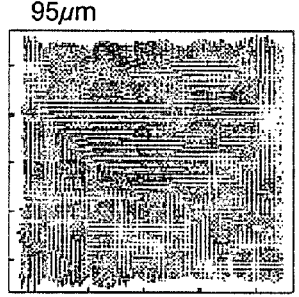
Figure 9H:
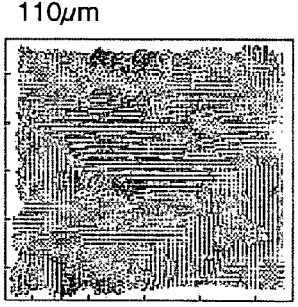
Figure 9I:
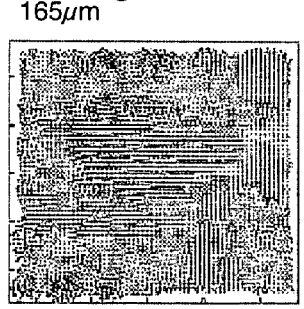
Figure 9J:
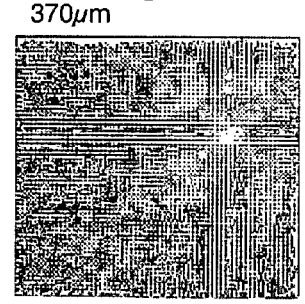
Figure 9K:
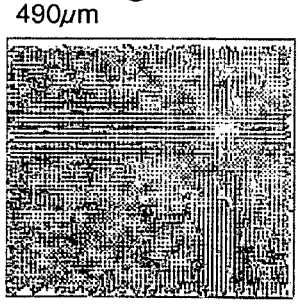
Figure 9L:
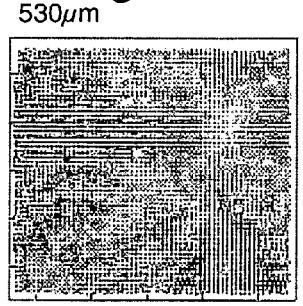

With increasing distance from the micronozzles, formed at the perfusing substrate 38, discrete, submerged jets, located near the center of the culture chamber 20, whose radial spreading (normal to the jet axe) at first intensified with the elevation now begin to decelerate in the transverse planes, as is shown in FIG. 9e, parallel to the perfusing substrate 38. This can be seen in FIGS. 9d-e through a reduction in the magnitude of the radial microjet velocity at higher distances from the perfusing substrate 38. Initially accelerating radial outflows (closer to the micronozzles) eventually begin to decay due to interaction with the zero momentum medium within the culture chamber 20 and the presence of spatial constraints imposed by surrounding jets and peripheral confinement (cylindrical enclosure 35 surrounding the cultured domain).

As jets penetrate further into the culture chamber 20, the dynamics of the flow changes to incorporate the influence of the target surface and peripherally located microchannel exits 37. Further reduction in jet streamwise momentum causes their turning from the nominally vertical trajectory and adjoining microjets begin to interact prior to their impingement on the surface of the FEP membrane 21, FIGS. 9f-i. Jet interference prior to impingement is likely to be enhanced when jets are closely spaced and when the distance between the nozzle and the impingement plate (nozzle-to-plate distance) is relatively large. In the presently disclosed flow configuration, this causes the outflows from a number of microjets to merge, FIGS. 9f and 9g, and, begin vectoring towards the perimeter of the cultured domain, FIGS. 9h and 9i, at elevations that are lower than that of the microchannel exits 37 that start at z=350 μm. This vectoring is influenced by the interaction of the induced wall jet (developing along the FEP membrane 21) with adjacent impinging microjets. Although the spatial arrangement of micronozzles in the array generally determines the way the microjets interact with each other, a strong wall jet originating from the centrally located stagnation zone, FIGS. 9j-l, governs the jet-to-jet interactions with increasing distances from the perfusing substrate.

While in single jet impingement, fully developed wall jet ultimately decays with increasing distance from the stagnation point due to its radial spreading and rising thickness, (see for example Deshpande M. D. et al. in 1982 J Fluid Mech 114:213-236), the horizontal acceleration of a developing, centrally located, wall jet here, continues longer due to merging of outflows from a number of microjets. In fact, this strong wall jet deflects the axe of microjets located further away from the center of the culture chamber 20 and their impingement is delayed or even prevented. The induced, biased convection towards the microchannel exits 37 is more pronounced in microjets located closer to the cylindrical enclosure 35 than those located closer to the center of the culture chamber 20. Therefore jets emanating closer to the center of the culture chamber 20 penetrate deeper into the cultured domain than those issuing closer to the enclosure walls 35, with the microjet axial flow trajectory reduction from the center towards the perimeter. While conventional culturing of brain slices in-vitro obtains poor long-term viability at the center of the slice, realized flow field in the present arrangement facilitates the control of cellular microenvironment by providing ample amounts of media to the most vulnerable part of the tissue located at the center of the culture chamber 20 with the nutrient concentration reducing towards the lateral sides. Overall, with increasing radial coordinate, the axial transport reduces and lateral transport increases within the cell culture life-support chamber 20, with significant convective enhancement in stagnation and wall jet regions over passive diffusion transport mechanism.

While single impinging jet exhibits three characteristic flow domains consisting of a free jet (not influenced by the target surface), stagnation and a wall jet region, the closely spaced array of impinging jets herein obtains a single, centrally located stagnation zone due to interactions among adjoining wall jets and the topology of exit flow. The sequence of images in FIGS. 9(j-l) confirm the merging of microjet outflows to yield a stagnation point near the center of the FEP membrane aerator 21, with the magnitude of the induced velocity (parallel to the perfusing substrate 38) reducing with the proximity to the impingement plane where it reaches zero. Miniature imperfections in the fabrication process influence the symmetry of the flow and enhance the fluid turning towards the part of the culture chamber 20 where the flow resistance is lower. In the present experiments, the presence of a center mark on the perfusing substrate 38 alters the location of the nominally centrally located stagnation region, so that it appears slightly off-center.

Measurements confirm that microjets issuing closer to the center of the perfusing substrate 38 penetrate deeper into the culture chamber 20 specifically targeting the most starved part of the tissue, while jet interactions and peripheral withdrawal of perfusate aid in the establishment of a complex 3-D flow within the culture chamber 20.

Temperature Measurements

The perfusion chamber 30 with the centrally forming culture chamber 20 is placed inside a cm-scale incubator 10 comprising a polystyrene enclosure 11 using nylon inserts such that biocompatible fluidic couplings pass through the bottom of the enclosure 11. The heated enclosure 11, which may have exemplary outer dimensions of 50×25×18 mm, contains a prescribed concentration of gases and maintains the temperature of the media and gases at about 37° C. The mini-incubator 10 contains a thermofoil heater 16 that heats the air inside the incubator 10. Gases necessary for cell metabolism enter the incubator 10 through its inlet port 12 (forced by a mini-blower, for example, outside the incubator 10) and leave through the outlet port 13. Externally located and controlled mini blowers 19 force the appropriate gas mixture (depending on the cultured tissue) over the heater 16 located on one side of the enclosure 11. In this configuration, gases blow directly onto the surface of the heater 16, and are predominantly heated by forced convection inside the mini-incubator 10. Heated gas warms the perfusion chamber 30 located downstream from the heater 16. The surface of perfusion chamber 30 and the culture chamber 20 reaches the thermal equilibrium with surrounding gas within the heated enclosure 11 so that the nutrient medium entering the incubator 10 through fluidic coupling inserted into media inlet 33 (FIGS. 4 and 5), warms up to the prescribed temperature, during the slow media advance towards the cell culture chamber 20.

In operation, the perfusion chamber 30 remains nearly isothermal so that the fresh nutrient medium injected into the culture chamber 20 through the perfusion substrate 38 reaches the desired temperature 37±0.2° C. within its fluidic inlet port 33 well before entering the cultured volume, with the heated length increasing linearly with the flow rate. For typical flow rates used in 3-D cell culturing the required heated length for the nutrient medium to reach desired temperature within the perfusion chamber 30 is sub-millimeter scale, i.e., 1 mm fluidic path through the inlet port 33, for example, is enough to warm the injected medium to a prescribed temperature. The temperature of the injected media just underneath the perfusion substrate 38 may be measured using a thermocouple that is connected to the temperature controller 18 to maintain the temperature in the range of 36.8-37.2° C. The PID controller 18 may be coupled to a DC switching solid-state relay to regulate the heat flux dissipated by the heater 16. Owing to its 7 µl of volume, culture chamber 20 and the entire perfusion chamber 30 facilitate temperature control due to relaxed working conditions and low time constants with negligible delays before parameters reach desired values. Small characteristic dimensions of the centimeter-scale incubator 10 result in negligible losses to the ambient. For example, for the heated enclosure 11 to be maintained at 37° C. heater 16 needs to dissipate about 1 W (based on losses to the ambient at 20° C.). Likewise, a fraction of a milliWatt is needed to warm the media to 37° C. at the volume flow rate of 7 µl/min (about 1 exchange/minute) with sub-millimeter scale heated length through the perfusion chamber 30.

Figure 10:
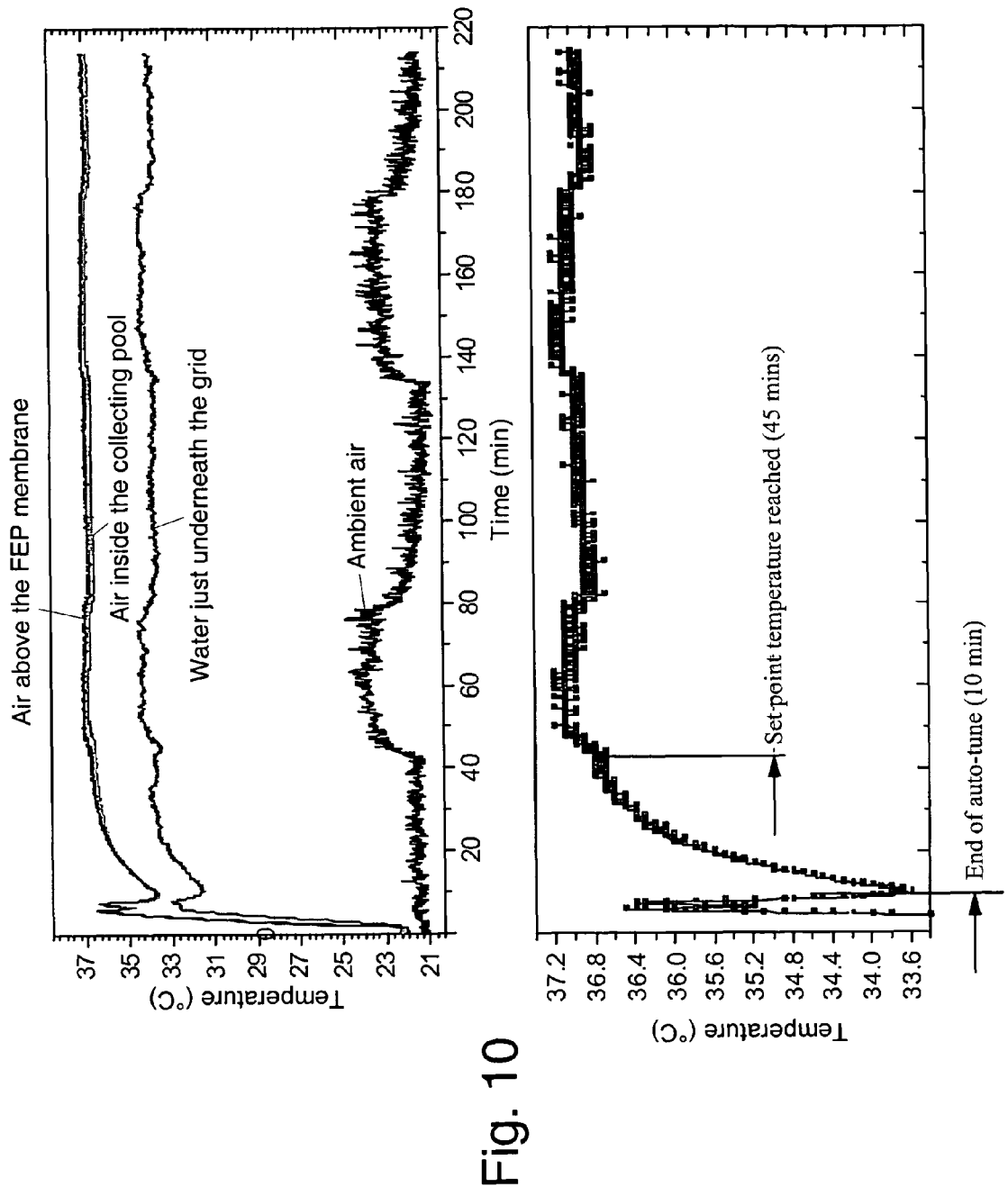
FIG. 10 shows graphs that illustrate thermocouple temperature measurements following an initial 10-minute long controller auto-tuning.
Figure 11:
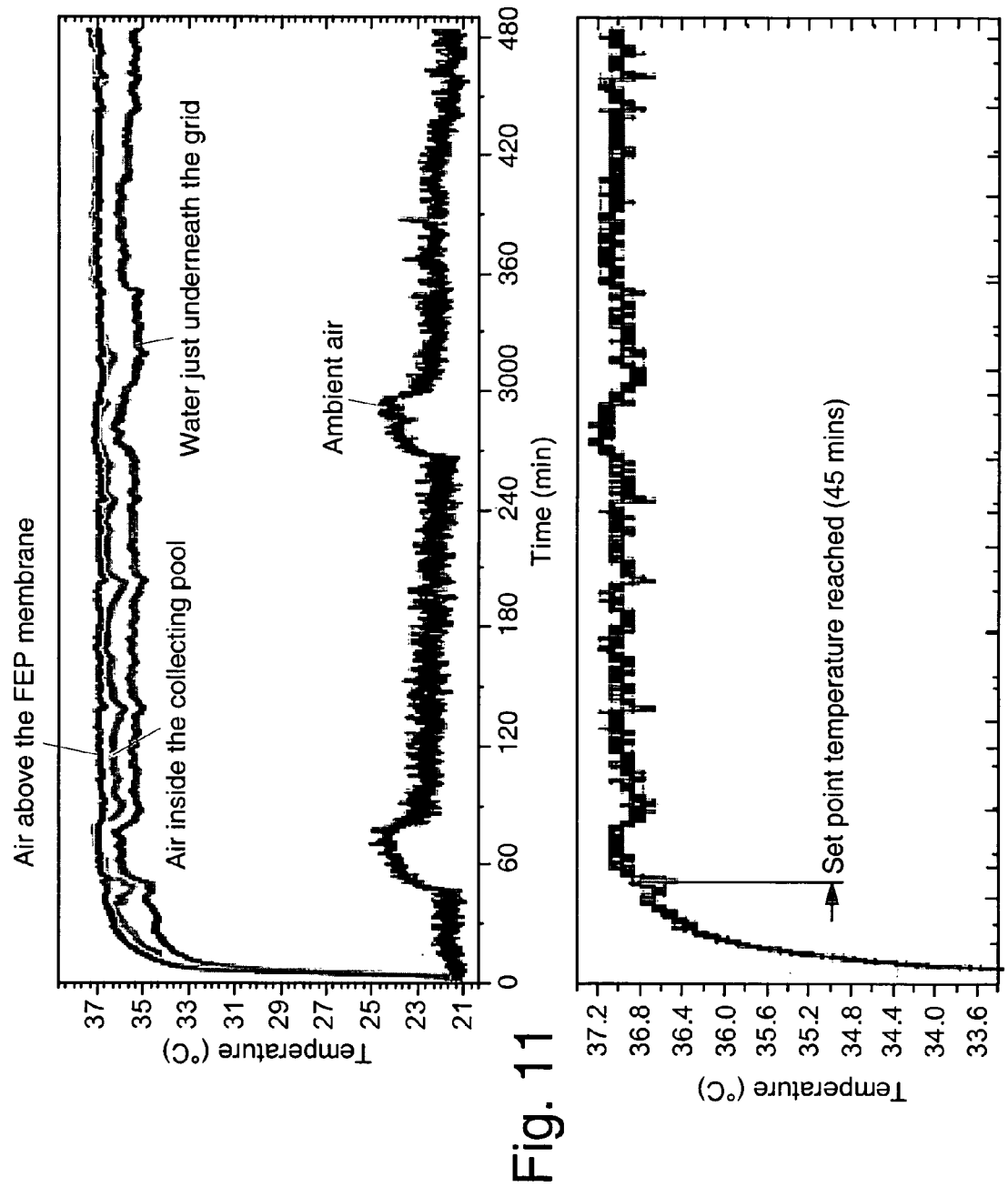
FIG. 11 shows graphs that illustrate temperature measurements while the incubator is in operation.

Temperature measurements inside the mini-incubator 10 may be taken at four locations, for example, using Fluke Hydra data acquisition unit with better than 0.1° C. temperature resolution. The temperature of the fresh nutrient medium is measured just before its injection into the culture chamber 20 (a thermocouple is placed immediately adjacent to the bottom side of the perfusion substrate 38 and routed through the media inlet port 33 via inlet tubing 24 and a small tee, and sealed). The temperature of the air inside the return flow collecting pool 41 may be measured by a thermocouple routed through the media outlet port 34. The temperature of air above the culture chamber 20 (i.e., above the FEP membrane 21) is also measured with the thermocouple routed through the side of the optically clear enclosure 11. The ambient air temperature outside the mini-incubator 10 is also measured. FIG. 10 shows graphs that illustrate thermocouple temperature measurements following an initial 10-minute long controller auto-tuning. FIG. 11 shows graphs that illustrate temperature measurements while the incubator is in operation.

For the PID controller 18 to maintain the temperature between a low and a high set point (37±0.2° C.), an auto-tune is performed during which an optimal set of constants (proportional, integral and differential) is found based on the thermal response of the system. After auto-tuning is finished, a low set point temperature is reached after about 45 minutes, as shown in FIG. 10. In operation, the controller 18 utilizes this set of parameters to maintain the temperature within a prescribed range in response to changes of ambient air temperature. Measurements taken during a 3-hour period, for example, demonstrate that the controller maintains the temperature of the media just before injection into the culture chamber 20 within the prescribed limits.

Measurements taken with a given set of parameters a few days later, as is shown in FIG. 11, demonstrate that after the initial warm-up period of the system, the temperature of the media remains within the set range over an 8-hour period during which measurements are taken. Thermocouple measurements reveal that the controlled media temperature just underneath the perfusion substrate 38 follows the temperature of the air inside the outer, collecting pool 41 where used media leaves the perfusion chamber 30.

A more uniform temperature distribution throughout the volume of the mini-incubator 10 may be easily obtained by insulating the exterior walls with a layer of foam-like tape, for example. This is also advantageous in preventing the visible light from entering the culture chamber 20 and disrupting the cells unless optical measurements are under way.

Multiple perfusion chambers 30 may be integrated within a single enclosure 11, for example, each with its own independent temperature controllers, or using the same controller, and gas sources. Several syringes can be used on each side of the syringe pump 19a moving block such that each perfusion chamber has an independent set of syringes for the simultaneous infusion of the culture medium and the withdrawal of catabolic waste products. This permits diagnostic testing of multiple samples in parallel without the possibility of cross contamination as perfusion chambers 30 are in fact microbe impermeable on the gas side. The volume flow rate of injected media can be different between adjacent perfusion chambers 30 by use of different pairs of syringes for particular chambers. For example, one culture chamber 20 can have exchange rate as much as 4 times higher, or more, than the other by choosing a syringe pair whose plungers have the surface area 4 times the surface area of plungers in another pair of syringes.

The scale-down from standard (refrigerator size) incubators to a cm-scale, portable, integrated, diagnostics incubator 10 obtains a remarkable physical enhancements such as the efficiency in heating or cooling the enclosures as they are miniaturized. This facilitates temperature control as heated or cooled centimeter-scale incubator obtains faster response times to temperature changes due to negligible inertia of an inherently miniature device, and, reduces costs associated power consumption.

Fabrication Methodology

Biocompatible and autoclavable, microfluidic perfusion chambers 30 may be rapidly prototyped using a process methodology that combines solid object printing and polymer replica molding (commonly referred to as the soft lithography, see for example Xia Y. and Whiteside G. M. in 1998 Angewandte Chemie 37:550-575). Custom or commercially available perfusion/cell attachment substrates are then sealed to the bottom of the cultured domain with a PDMS prepolymer, and cured.

Figure 12:
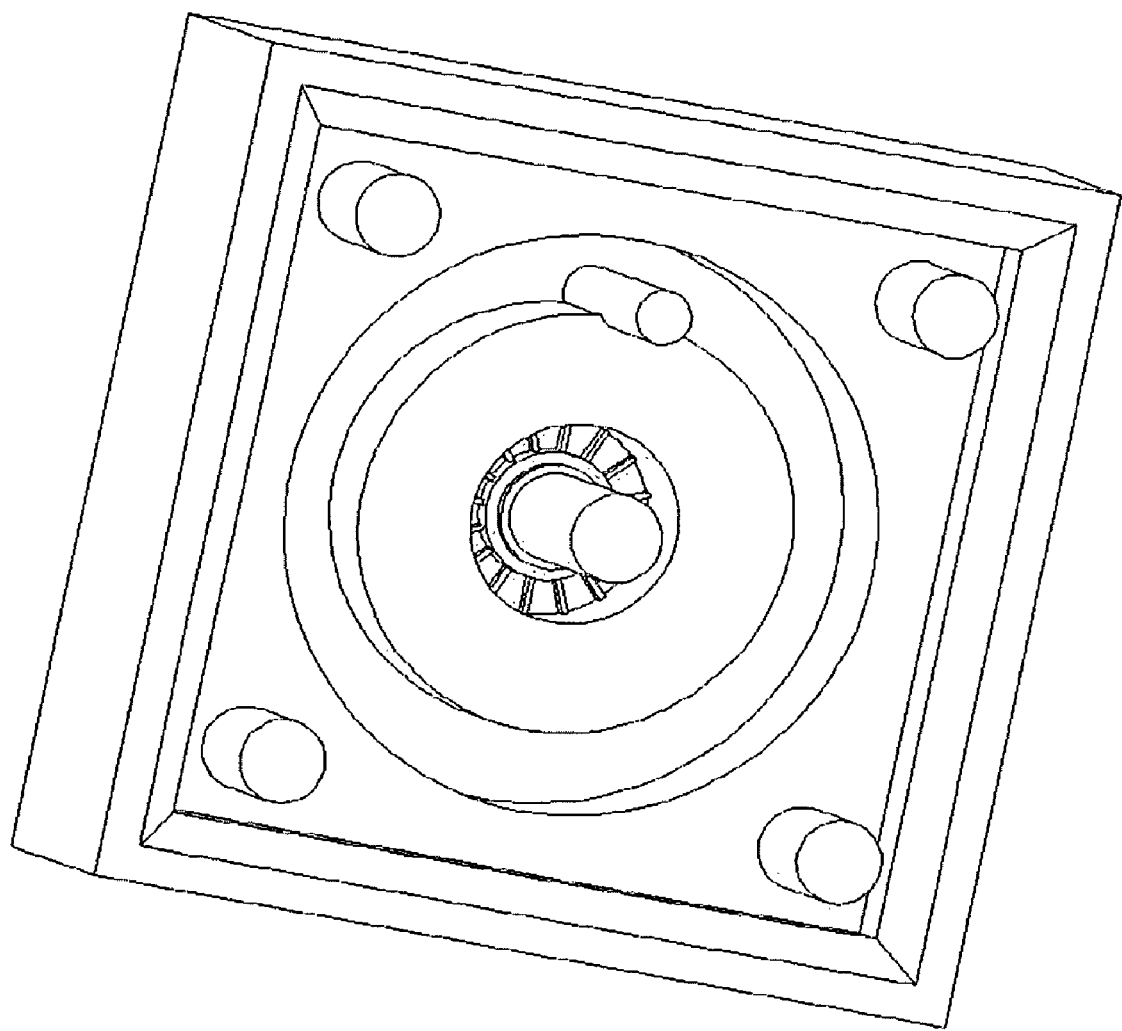
FIG. 12 illustrates a disposable thermoplastic master formed by solid object printing for use in elastomeric molding of perfusion chambers.

Disposable masters for the elastomeric molding, as is shown in FIG. 12, are produced by solid-object printing (SOP) of an organic thermoplastic (wax-like) polymer that solidifies upon extrusion based on a defined 3-D CAD mold, for example. This convenient inkjet printing tool eliminates the need for expensive cleanroom facilities, and, unlike inherently planar 2-D photolithographic techniques, obtains truly 3-D objects whose feature resolution is 86 $\mu$m. Following the mold design phase, production is virtually hands free as printer fabricates the masters, layer by layer, directly onto a platform without the use of masks. In a few hours over fifty wax molds may be fabricated in a single print. The resolution of the commercially available Thermojet printer (3D Systems, Valencia, Calif.) used herein is 300×400×600 dpi, i.e. 85, 64 and 24 $\mu$m in x, y, and, z respectively. For the majority of microvascular systems used in bioengineering, this yields sufficient feature details and permits quick completion of several design iterations, fabrication and testing at a low cost. The smallest extruded features of the perfusion chamber mold is a positive relief for the elastomeric molding of 150 $\mu$m wide and 350 $\mu$m deep microchannels that are reproduced faithfully owing to the excellent shape conforming properties of the PDMS prepolymer.

Upon extrusion of the perfusion chamber molds, a 10:1 mixture of the PDMS pre-polymer base and cross-linking agent (SYLGARD 184 Silicone Elastomer Kit, Dow Corning, Midland, Mich.) is poured into the wax template, cured at room temperature for 48 hours, and, peeled off. The use of mold release agents was deemed unnecessary owing to favorable surface chemistries of materials in contact. However, to facilitate the release of cured polymer replicas from deep disposable molds, the top of their sidewalls are fabricated at a 45° angle. This ensures that the upper most layer of the polymeric PDMS material is entirely peeled-off, thus allowing good grip in stripping subsequent layers. During detachment, vertical columns that correspond to fluidic connections in the finished perfusion chamber 30 usually break from the mold base so that thermoplastic templates cannot be reused. Posts that remain within released replicas are simply pushed through the cast openings within PDMS using a thick needle. Depending on size, objects entrapped within released elastomer can be removed by either heating the replicas to melt the thermoplastic material followed by suction of the latter, or, in case of truly micron scale features by dipping them in organic solvents (e.g. OS-20 low molecular weight siloxane, Dow Corning, Midland, Mich.), thus causing the temporary swelling of PDMS and the release of trapped components.

To further reduce the prototyping costs, disposable, thermoplastic masters can be replaced by reusable, polymeric, master molds. Reusable templates can be fabricated using a "sandwich method", i.e., by encapsulating the prepolymer within an extruded box, and, by inserting the cast PDMS perfusion chamber 30 into the box face down so that its base acts as a box lid. This enclosure box may be extruded using a 3-D printer such that the model interior dimensions correspond to the outer dimensions of the PDMS perfusion chamber 30. During insertion of the PDMS perfusion chamber 30 into the box, the excess prepolymer leaves the mold through fluidic openings located on the base of the perfusion chamber 30 (box lid). The procedure is straightforward and it takes only two sacrificial thermoplastic molds to fabricate a single reusable PDMS master.

Favorable PDMS Material Properties

Polydimethylsiloxane (PDMS) is a rubbery, biologically compatible, microfabrication compatible, silicone elastomer that is low-cost, and generally non-toxic, non-flammable, thermally stable, chemically inert, optically clear, permeable to gases including oxygen and carbon dioxide and almost impermeable to water, see for example, Ng J. M. K. et al. in 2002 Electrophoresis 23:3461-3473. It conforms to submicron features with no discernible pattern degradation or surface distortion upon common biological handling and represents the material of choice for versatile biological and medical applications (see for example, McDonald J. C. et al. in 2002 Acc Chem Res 35:491-499; or Whitesides G. M., et al. in 2001 Ann Rev Biomed Eng 3:335-373). PDMS properties offer substantial advantages over fabrication methods in hard materials. Molding of 3-D structures in PDMS is inexpensive, easy, and a versatile method of making complex geometries. The sealing of fluidic devices, coupling of components, packaging and interfacing of integrated systems is fairly straightforward to employ in PDMS owing to its elasticity, watertight sealing properties and low electrical conductivity.

The modular design of the perfusion chamber 30 enables the use of commercially available or custom made substrates, thus introducing specific topography, flow characteristics and surface chemistry intended for particular set of experiments. Besides gold, PDMS, SU-8 photopolymer, polymethyl methacrylate (PMMA), and other materials may be used as perfusion/growth substrates upon certain surface treatments that render the surfaces cytophilic. Specifically, the ease of PDMS topographical and chemical patterning makes it an ideal candidate for perfusion substrate whose shape, texture and surface chemistry can be adjusted to promote cellular adhesion. Pulsed plasma deposition of allylamine on hydrophobic polydimethyl-siloxane (PDMS), for example, creates cytophilic cell adhesion substrates that can be sterilized using steam autoclaving and re-used for several cycles (Harsch A, et al. in 2000 J Neurosci Meth 98:135-144). Attachment and growth of cultured neurons can be manipulated using microcontact printing methods that permit the deposition of thin layers of various organic materials on PDMS with varying degree of organized architecture. Selective patterning of PDMS substrates may also be necessary to confine cell growth to particular regions within the culture chamber 20. Silanizing oxidized PDMS with an amino-terminated silane (aminopropyltriethoxysilate) provides a reactive surface for a bifunctional cross-linker for protein attachment (Bernard A., et al. in 2001 Nat Biotechnol 19:866-869). A similar technique can be employed to attach amino-terminated polyethylene glycol (PEG) to make the surface stable against surface rearrangement and hydrophilic for days in air, e.g., Donzel C., et al. in 2001 Adv Mater 13:1164-1168. Bio-fouling, a non-specific protein adsorption to surfaces such as the interiors of microbore tubes or microchannels, for example, represents a common problem in microfluidics as it eventually leads to device clogging. Grafting a poly(ethylene glycol)di-(triethoxy)silane onto an oxidized PDMS surface, the surface of PDMS becomes permanently hydrophilic with reduced bio-fouling properties, see for example Papra A. et al. in 2001 Langmuir 17: 4090-4095.

Enabling Qualities and Empowering Functionalities of the Centimeter-Scale Diagnostics Incubator with Integrated Perfusion The disclosed instrumented, portable, centimeter-scale incubator 10 represents a striking departure from the standard culture environment posing virtually no limits for field applications with the convenience of being compact, and, flexibility in design and operation that allows its integration into a more robust totally integrated systems. Hence, advantages of the miniaturized incubator 10 include (1) reduced size of the functional device, (2) flexibility in design, (3) minimized response times in pharmacological and biochemical analyses owing to microliter volume culture chamber 20, (4) low expenditures associated with the amount of used reagents, (5) reduced production of toxic waster products, (6) decreased requirements for power, (7) reliable and reproducible operation owing to relaxed operating conditions associated with superior control of physical and chemical parameters in small scale devices, (8) increased speed of analyses, (9) the ability to operate in parallel a number of perfusion chambers 30 onboard a single centimeter-scale incubator 10, (11) low-cost devices resulting from fabrication of all components onboard a single, disposable platform 30, (12) optical, electrical and fluidic accessibility, (13) facile fabrication, packaging, integration and interfacing, and, (14) portability.

A reduced-to-practice mini-incubator 10 enables simultaneous optical, fluidic and electrical interfacing, and data acquisition, in a controlled environment prescribed by the temperature, concentration, and flow rate of gases, nutrients or other relevant substances. In an exemplary embodiment, the temperature of the media inside the incubator 10, just before injection into the culture chamber 20, is controlled at 37±0.2° C. Associated infrastructure can support a number of mini-incubators 10 with their separate perfusion chambers 30. In-situ diagnostic testing may be performed without disruption of cultured tissue within separate mini-incubators 10, thereby reducing the chances of contamination.

Growing needs to miniaturize and scale-down cell cultures and their microenvironments in vitro from multi-well screening plates to disposable cell assays for biochemical analyses for example, in an environment that preserves the culture viability and allows in situ monitoring of their physiology, small-scale diagnostic incubators with integrated perfusion become necessary to manipulate the cellular environment down to molecular or cell level. Although surface forces become dominant following the scale-down in size of conventional systems, the similarities in physical and chemical parameters are generally preserved resulting in analogous biological behavior. Following the scaled-down inertia of the system reduces leading to faster response times to chemical stimuli and physical changes. This, in turn, offers unprecedented control of biological processes due to negligible time delays before parameters reach desired, steady state values and gives an insight into a real time dynamics of cellular responses to stimuli. A reduction in characteristic length scale usually results in relaxed operating conditions for sensors and actuators, often eliminating excessive hardware and high power associated with large-scale systems. Hence, unlike scaling up, scaling down simplifies incubator operation and control thereby substantially lowering costs, allowing parallel processing of multiple samples, and provides higher accuracy and reproducibility of performed assay analyses.

Compared to conventional culture tools using Petri dishes or multi-well screening plates, the centimeter-scale incubator 10 with its microliter volume perfusion platform 30 offers greater control over the cellular microenvironment. Using relatively small number of cells at a high plating density, cellular response to rapid changes in bathing medium composition, application of drugs, or the changes in the extracellular ionic concentration governing the cellular excitability can be accurately controlled and easily altered. While relevant scientific studies have been hindered by diffusion limited supply of the nutritive substances and gases necessary for cellular metabolism, the perfusion chamber 30 exposes the cells to continuous flow of media with rapid exchange rates to ensure plethora of nutrients and prevent the metabolic culture decay. Thus, in the centimeter-scale incubator 10, 3-D cultures can be easily maintained in vitro over extended periods of time with sufficient concentration of nutrients and gases at an optimal value of acidity and temperature so that the humoral states are not altered during the course of an experiment.

Concurrent, long-term, bio-culturing with in-situ diagnostics and sample preservation has numerous benefits. Controllable field culturing (away from major laboratories), tissue growth and analysis on a microscope stand, controllable injection of media and trophic factors, biomonitoring and biosensing are just a few applications where the mini-incubator 10 with its integrated perfusion chamber(s) 30, optical and electrical accessibility are desirable. While perfusion chambers with and without environmental control are available, e.g., neuronal perfusion, the utility and widespread use of these devices is often hindered by metabolically inadequate capillary action nutrient delivery, and, their inadaptability to be modular and address a wide range of tasks at a reasonable price. The design of the biocompatible perfusion chamber 30 ensures forced convection closed-loop continuous infusion of nutrients and withdrawal of waste with enhanced exposure to gases necessary for cell metabolism to extend the culture longevity beyond that achieved in large-scale incubators or small incubation baths. Disposable or steam autoclavable perfusion chamber 30 can be easily re-configured to meet a particular demand with a new device in hand in a matter of hours without compromising its simplicity.

The modular and low-cost design of mini-incubator 10 facilitates plug-in functionality of various building blocks that can be easily integrated (e.g., mixing chambers, nano-volume multi-port controllable injectors, microelectrode arrays, sensors, etc.) and allows operation either in full-scale laboratories or in the field, providing a portable, fully self-contained biological workstation. For example, perfusion chamber 30 may enable temporal and spatial control of injected agents in addition to continuous delivery of the cell culture media, Customized sample holders can be fitted as necessary with fluidic and electrical connectivity to facilitate in situ sample manipulation and diagnostics with negligible risk of contamination. The modular infrastructure can support a number of mini-incubators 10 with their separate perfusion chambers 30 that can be easily plugged in and out of a centralized system, providing maximum flexibility in experimental design and minimal capital expenditure. In-situ diagnostic testing may be performed within separate incubators 10, eliminating disruption of other cultured tissue and thereby dramatically reducing the chances of contamination. Various workstation designs may be constructed and inexpensively customized to allow for concurrent optical, fluidic and electrical interfacing to permit full experimental control, including data acquisition and individual sample preservation.

Thus, in summary, the incubator workstation 10 has optical, environmental and fluidic accessibility and enables simultaneous culturing and analyses on a microscope stand. Integrated, actively controlled, perfusion chamber 30 utilizes forced convection for intercellular nutrient supply and gas exchange thereby allowing the studies of thicker tissue slices and dissociated, high-density, three-dimensional (3-D) cultures over extended periods of time. Miniature cell culture life support chamber 20 (about 7 μl) offers relaxed operating conditions with superior environmental control and reduced expenditures associated with harvesting, culture preparation, the amount of used reagents and power consumption. A number of perfusion chambers 30 can be integrated onto a common platform for high-throughput culture screening with reduced risk of contamination. Superior culture aeration is achieved two-fold: (i) through an optically clear, microbe and water impermeable membrane 21 placed over the top of the culture chamber and via (ii) separate in-line venting bubble trap 26. A thin membrane 21 that encapsulates the perfusion chamber 30 enables efficient gas exchange and keeps the tissue moist in a sterile environment. It further reduces the risks of contamination by allowing the culturing in non-humidified incubators. The in-line aerator 26 ensures the equilibrium of the nutrient medium with the gas environment, via semi-permeable membrane 27, before being injected into the culture chamber 20. This device 26 also serves as an autoventing bubble trap that prevents the bubbles from ever reaching the perfusion chamber 30. The use of in-line aerator 26 eliminates the need for a separate enclosure to equilibrate the media and a bubble trap to purge the bubbles, thus greatly simplifying the design and enabling development of cost-efficient compact devices. Spatially 42 or temporally varying concentrations of injected substances 41 into the culture chamber 20 can be dynamically controlled. Additional functionalities including but not limited to glucose consumption, pH or dissolved $O_2$ sensing and control 18a (FIG. 1) can be easily integrated into the device 30. Shape conforming and contact sealing properties of the polydimethylsiloxane polymer used in the fabrication of a perfusion chamber 30 enable straightforward fabrication of complex three-dimensional structures, sealing of devices, coupling of various microfluidic and electrical components, packaging and integration into functional systems that can be easily interfaced with the macro world, see for example Beebe D. J. et al. in 2000 Proc Natl Acad Sci USA 97: 13488-13493; Chabinyc M. L. et al. in 2001 Anal Chem 73: 4491-4498; or Zanzotto A. et al. in 2004 Biotechnol Bioeng 87:243-254.

The modular design with versatile plug-in-functionalities can be tailored to specific use and omitted in particular application. These functionalities include but are not limited to: microfluidics, e.g. micropumps, valves, mixers and microinjectors; introduction of spatially or temporally varying concentration gradients of injected substances into the culture chamber 20; the integration of microelectrode arrays for physiological studies; biosensors for detection and control of small molecules (oxygen, pH, glucose) and large molecules (immunosensors); the capabilities of cooling below the ambient temperature to preserve the tissue for example; or the packaging of a larger number of culture chambers onto a common platform.

Increasing demands for miniature, disposable cellular essays for long-term pharmacological or biochemical studies and tissue engineering require perfused, controllable cellular microenvironments. Controllable features include but are not limited to: the adjustable shape and texture of the cell culture life support chambers, specific surface chemistry or protein adsorption, and, tunable topography of extracellular matrices and chemically patterned microfabricated scaffolds that can only be realized in a microfabrication compatible, low-cost, mass produced, dynamic perfusion platforms. These requirements come in parallel with the needs to reduce the costs associated with the amount of used specimen, biochemicals, disposal of waste, excessive hardware associated with large-scale systems, power consumption, and, repeated analyses due to metabolic failures in the absence of functional vasculature and blood supply to the tissue upon harvesting.

Compared to conventional culture tools using Petri dishes or multi-well screening plates, the disposable or autoclavable culture chamber 20 measures about 7 μl in volume and offers superior control of the cellular microenvironment, see for example Vukasinovic J. et al. in 2006 Proceedings of the 2006 ASME Summer Bioengineering Conference. Owing to the facile fabrication methodology, straightforward integration and packaging, perfusion chamber 30 and the miniature incubator 10 can be easily modified to meet different requirements. For example, the ultimate challenge of diagnostic cell assays is to incorporate biosensors and control loops to monitor temperature, humidity, pH, oxygen or ionic concentration in a perfused system with adjustable, spatially selective, steady state or temporally varying, velocity or concentration gradients, all within a common platform that contains a large number of cell arrays ready for fundamental studies, optical diagnostics, and, intra- or extracellular stimulation and recording. Thus this constitutes one of the many applications where a centimeter-scale, diagnostics incubator 10 with the integrated perfusion chamber 30 can be used.

Recent interest in totally integrated systems should eventually result in development of inexpensive, microfabricated devices with automated dissociation, cellular manipulation and diagnostics, see for example Prokop A. et al. in 2004 Biomed Microdevices 6:325-339. These computer-controlled Microsystems will incorporate perfusion chambers, incubators, sensors, laminar flow hoods and hardware related to cell feeding, counting, etc. on a single, seemingly disposable, platform. The disclosed centimeter-scale incubator 10 with integrated perfusion is an example of how conventional (refrigerator size) incubators can be scaled down, and how their utility can be empowered with fluidic functionality and optical accessibility. Other advantages of the scale-down include reduced response times to physical changes and chemical stimuli, higher repeatability of performed analyses, reduced number of cells at high plating densities, low cost with minimal volume requirements, and, the possibility for parallel processing of many samples onboard a single disposable platform.

As mentioned in the Background section, the dominant mode of mass transport in commercially available incubation baths remains diffusion and/or capillary action to passively augment the supply of media and oxygen to the tissue that eventually runs down metabolically. However, to meet and exceed the metabolic requirements for nutrient delivery and catabolic waste removal, mass transport by pure diffusion becomes insufficient and demands a convective enhancement for an adequate, dynamic, long-term control of the culture condition.

Such enhancement is achieved in the novel, perfusion chamber 30, where convection based intercellular mass transport can be actively controlled and problems associated with the flow perturbations at the interface (Haas chamber), for example, or the floating of the tissue and the injection of drugs (Zbicz chamber) completely eliminated. Recent experiments corroborate the utility of forced convection interstitial nutrient delivery obtained in the perfusion chamber setting 30. An efficient circulatory system disclosed herein facilitates the studies of thicker organotypic cortical brain slice cultures as demonstrated by Rambani K. et al. in 2006 at the Society for Neuroscience 36th Annual Meeting, Neuroscience 2006. The integrated membrane 21 and an in-line aerator 26 enable gas transport from both sides of the brain slice.

The perfusion chamber 30 not only obtained high viability of perfused cortical slices, but also the perfusion of nutrient medium in larger scale chambers of a similar design proved to be a productive tissue engineering setting enabling the growth of high-density, physiologically more credible, 3-D tissue-equivalent constructs. Perfused neuronal-astrocytic co-cultures grown in an extracellular matrix at cell densities close to that of the brain tissue (10,000 cells/mm$^3$) exhibited over 90% viability throughout their thickness (500-750 µm) while non-perfused, sister-cultures evidenced widespread death as described by Cullen D. K. et al. in 2006 at the 28TH Annual International Conference IEEE Engineering Medicine and Biology Society, and by Cullen D. K. et al. in 2006 at the Society for Neuroscience 36th Annual Meeting, Neuroscience 2006. Note that culture models consisting of multiple cell types, such as neuronal/astrocytic co-cultures, for example, closer approximate the heterogeneity of the in vivo tissue. In particular, the heterogeneity of the nervous system is better represented through the physical support and the metabolic coupling between neurons and astrocytes, e.g. Tsacopoulos M. et al. in 1996 J Neurosci 16:877-885, or, Aschner M. in 2000 Neurotoxicology 21:1101-1107.

One of the empowering aspects of the biocompatible perfusion chamber 30 integrated within a centimeter-scale diagnostic incubator 10 lies in its straightforward adaptability to various application challenges by incorporating versatile microfluidics and MEMS functionalities with superior control of pertinent cellular microenvironment than that achieved in standard, multi-well screening plates, Petri dishes, or Haas- or Zbicz-top incubation baths. Other enabling qualities include the ability to integrate multielectrode arrays or biosensors to monitor physiological functions down to cellular level, and, generate complex, steady state e.g. Dertinger S. K. W. et al. in 2001 Anal Chem 73:1240-1246, or, temporally varying gradients of biologically active substances using microfluidic networks and different modes of perfusion. By actively controlling perfusion, the nature of cell feedings can be radically changed to enhance haptotaxis for example, e.g. axonal outgrowth and path finding along gradients of diffusible substances containing chemoattractants or repellents, e.g. Baier H. et al. in 1991 Science 255:472-475. Perfusion can be continuous, cyclic in a periodic or an aperiodic fashion following a specific control curve, push/pull, and could involve the re-use of the spent media for subsequent feedings in cases where high-exchange rates may lead to depletion of trophic factors secreted by the cells to support their own growth. Furthermore the dynamic perfusion system 30 facilitates the control over the composition of the bathing medium, its temperature, pH and the degree of oxygenation. Using the optical isolation of a pocket-size incubator 10, non-invasive sensing methods may be employed in measuring the amount of dissolved oxygen and pH using either the commercially available sensor foils, or lifetime fluorescence of oxygen and pH-sensitive dyes. In either case the sensing infrastructure remains outside the incubator enclosure, thus keeping it inexpensive, facile to fabricate, and, therefore disposable. The centimeter-scale integrated diagnostics incubator 10 is thus portable. Relevant hardware (pump, fan, controllers) may be battery operated and the appropriate gas mixture supplied in a small bottle. The same incubator 10 can be used to preserve biological specimen at a temperature that is below the ambient temperature by replacing the resistive heater with a miniature thermoelectric heat pump.

Portable, optically accessible, centimeter-scale, integrated diagnostics incubator for use in biological culturing with actively controlled forced convection perfusion has been disclosed. It is to be understood that the above-described embodiments are merely illustrative of some of the many specific embodiments that represent applications of the principles discussed above. Clearly, numerous other arrangements can be readily devised by those skilled in the art without departing from the scope of the invention.

What is claimed is:

1. Diagnostic incubator apparatus comprising:
an optically accessible enclosure having a plurality of inlet and outlet ports;
an environmental control element disposed within the enclosure that is couplable to an external controller;
a perfusable sample chamber disposed within the enclosure;
an optically transparent semi-permeable membrane aerator encapsulating the perfusable sample chamber; and
convection apparatus that enables forced convection of a selected gas and/or liquid medium through the optically accessible enclosure and the perfusable sample chamber.

2. The apparatus recited in claim 1 further comprising:
apparatus that maintains prescribed pressure within the optically accessible enclosure and the perfusable sample chamber.

3. The apparatus recited in claim 1 further comprising:
apparatus for establishing spatially varying, temporally invariant concentration gradients of injected agents within the perfusable sample chamber.

4. The apparatus recited in claim 1 further comprising:
apparatus for establishing spatially invariant, temporally varying concentration gradients of injected agents within the perfusable sample chamber.

5. The apparatus recited in claim 1 further comprising:
apparatus coupled to selected inlet and outlet ports for forcibly convecting a selected medium through the enclosure and perfusable sample chamber at a volume flow rate that is sufficient to expose a sample disposed within the perfusable sample chamber to a concentration of the medium that is sufficient to inhibit sample deterioration.

6. The apparatus recited in claim 1 further comprising:
an in-line venting device coupled between a selected inlet port and the perfusable sample chamber that (1) equilibrates the liquid medium with the selected gas and pH environment prior to its injection into the perfusable sample chamber, and (2) removes gas bubbles from the liquid medium prior to its injection into the perfusable sample chamber.

7. The apparatus recited in claim 1 wherein the perfusable sample chamber comprises:
- a perfusion substrate containing orifices having a selected two-dimensional or three-dimensional topology;
- one or more inlet ports in communication with the sample chamber via one or more perfusion substrates;
- a return flow collection chamber in communication with the sample chamber; and
- one or more outlet ports coupled to the collection chamber.

8. The apparatus recited in claim 1 further comprising:
- a plurality of membrane aerated perfusable sample chambers disposed within the enclosure; and
- a plurality of convection apparatus coupled to respective perfusable sample chambers for forcibly convecting predetermined medium through each of the respective perfusable sample chambers.

9. The apparatus recited in claim 1 which has a size and is configured for placement on a microscope stand for manipulation underneath a microscope objective.

10. The apparatus recited in claim 1 which is a hand-held portable apparatus adapted for diagnostic field analyses, sampling, sample preservation, and culturing of samples, with negligible risk of contamination or cross-contamination of the samples, which enhances long-term viability of incubated samples, and enables culturing of brain slices on the order of 700 μm thick over at least a 5 day period in vitro.

11. The apparatus recited in claim 1 which is a hand-held, portable, battery operated, apparatus adapted for diagnostic field analyses, sampling, sample preservation, and culturing of samples, with negligible risk of contamination or cross-contamination of the samples.

12. The apparatus recited in claim 1 wherein the perfusable sample chamber comprises a culture chamber, a perfused culture chamber, a chemotaxis chamber, a haptotaxis chamber, or a sample preservation chamber.

13. A method for incubating a sample comprising:
- disposing a sample in a perfusable sample chamber that is encapsulated by an optically transparent semi-permeable membrane aerator;
- disposing the perfusable sample chamber and sample in an optically accessible enclosure;
- forcibly convecting a selected gas through the enclosure and/or perfusable sample chamber and sample;
- forcibly convecting a selected medium through the perfusable sample chamber and sample to supply a high concentration of the medium throughout the sample;
- continuously removing excess amounts of the medium and waste products generated by the sample; and
- forcibly convecting heat within the optically accessible enclosure to maintain a desired sample temperature.

14. The method recited in claim 13 further comprising:
- circulating the selected gas through the enclosure and/or perfusable sample chamber in a closed loop manner, and circulating the selected medium through the perfusable sample chamber in a closed loop manner.

15. The method recited in claim 13 further comprising:
- circulating the selected medium through the perfusable sample chamber in a continuous, closed loop manner; and
- removing depleted or used medium and waste products from the perfusable sample chamber.

16. The method recited in claim 15 further comprising:
- collecting and analyzing the used medium, sample secreted matter and/or waste products.

17. The method recited in claim 15 further comprising:
- recycling used medium through the perfusable sample chamber.

18. The method recited in claim 17 further comprising:
- controlling the ratio of newly added medium to recycled medium in the perfusable sample chamber.

19. The method recited in claim 13 further comprising:
- controlling the amount of medium circulated through the perfusable sample chamber using a controller that is external to the optically accessible enclosure.

20. The method recited in claim 13 further comprising:
- programmably injecting one or more predetermined biological or chemical agents into the perfusable sample chamber.

21. The method recited in claim 13 further comprising:
- programmably injecting one or more predetermined agents concomitant with continuous infusion of another agent into the perfusable sample chamber.

22. The method recited in claim 13 further comprising:
- programmably injecting one or more predetermined biological or chemical agents into the perfusable sample chamber; and
- removing selected agents from the perfusable sample chamber.

23. The method recited in claim 13 further comprising:
- maintaining pressure within the optically accessible enclosure, sample chamber and sample at a desired level.

24. The method recited in claim 13 further comprising:
- controlling the volume flow rate of the selected medium through the perfusable sample chamber.

25. The method recited in claim 13 further comprising:
- establishing spatially varying, temporally invariant concentration gradients of injected agents within the perfusable sample chamber.

26. The method recited in claim 13 further comprising:
- establishing spatially and temporally varying concentration gradients of injected agents within the perfusable sample chamber.

27. The method recited in claim 13 further comprising:
- injecting predetermined agents into the perfusable sample chamber using separately addressable fluidic inputs, interfaced outside the optically accessible enclosure.

28. The method recited in claim 13 further comprising:
- forcibly convecting a medium equilibrated within the optically accessible enclosure and the gas at volume flow rates that enable culturing of thick organotypic brain slices in vitro over an extended period of time.

29. The method recited in claim 13 further comprising:
- actively controlling the convective, interstitial exchange rate of equilibrated media to prevent metabolic decay of the sample.

30. Perfusion apparatus for perfusing a sample, comprising:
- a perfusion substrate comprising orifices having a selected two-dimensional or three-dimensional topology;
- a sample chamber for structurally supporting the sample and enabling its attachment to the perfusion substrate;
- one or more inlet port ports in communication with the sample chamber through the perfusion substrate;
- a return flow collection chamber in communication with the sample chamber;
- one or more outlet ports coupled to the collection chamber; and
- an optically transparent, gas permeable, microbe impermeable and substantially water impermeable membrane encapsulating the perfusion platform.

31. The apparatus recited in claim 30 wherein the perfusion substrate comprises a screen or grid having a selected porosity, selected two-dimensional or three-dimensional topography, or selected surface chemistry for manipulating flow conditions and/or sample adhesion to the perfusion substrate, where the substrate comprises one or more internal surfaces of the sample chamber.

32. The apparatus recited in claim 30 wherein the perfusion substrate comprises a material that promotes or inhibits adhesion of a particular constituent of the sample.

33. The apparatus recited in claim 30 wherein the sample chamber contains three-dimensional extracellular matrices, microfabricated patterns, or scaffolds that promote cellular growth and attachment, direct cell growth, or act as fluidically functional injection sites.

* * * * *

UNITED STATES PATENT AND TRADEMARK OFFICE
CERTIFICATE OF CORRECTION

| | | |
|---|---|---|
| PATENT NO. | : 7,855,070 B2 | Page 1 of 1 |
| APPLICATION NO. | : 11/483126 | |
| DATED | : December 21, 2010 | |
| INVENTOR(S) | : Jelena Vukasinovic and Ari Glezer | |

It is certified that error appears in the above-identified patent and that said Letters Patent is hereby corrected as shown below:

Column 7, line 15, delete "opening is formed" and replace with --opening 36 is formed--.

Column 11, line 24, delete "perufsing substrate 38" and replace with --perfusing substrate 38--.

Column 11, line 29, delete "pefusing substrate 38" and replace with --perfusing substrate 38--.

Column 13, line 1, delete "While single impinging jet" and replace with --While a single impinging jet--.

Column 15, line 16, delete "obtains a remarkable physical enhancements" and replace with --obtains remarkable physical enhancements--.

Column 15, lines 41-42, delete "as printer fabricates" and replace with --as a printer fabricates--.

Column 18, line 29, delete "ensure plethora of nutrients" and replace with --ensure a plethora of nutrients--.

Column 20, line 42, delete "Thus this constitutes" and replace with --Thus, this constitutes--.

Column 20, lines 49-50, delete "computer-controlled Microsystems" and replace with --computer-controlled microsystems--.

Column 24, line 55, delete "inlet port ports" and replace with --inlet ports--.

Signed and Sealed this
Thirteenth Day of September, 2011

David J. Kappos
*Director of the United States Patent and Trademark Office*